United States Patent
Wada et al.

(10) Patent No.: US 8,470,987 B2
(45) Date of Patent: Jun. 25, 2013

(54) PROTECTIVE GROUP FOR SYNTHESIS OF RNA AND DERIVATIVE

(75) Inventors: Takeshi Wada, Chiba (JP); Mamoru Shimizu, Chiba (JP)

(73) Assignee: Chiralgen, Ltd., Kagoshima (JP)

( * ) Notice: Subject to any disclaimer, the term of this patent is extended or adjusted under 35 U.S.C. 154(b) by 119 days.

(21) Appl. No.: 12/882,390

(22) Filed: Sep. 15, 2010

(65) Prior Publication Data

US 2011/0178284 A1    Jul. 21, 2011

Related U.S. Application Data

(60) Provisional application No. 61/242,877, filed on Sep. 16, 2009.

(51) Int. Cl.
C07H 19/00    (2006.01)
C07H 21/00    (2006.01)

(52) U.S. Cl.
USPC ................................. 536/22.1; 536/25.3

(58) Field of Classification Search
USPC ............................................ 536/22.1, 25.3
See application file for complete search history.

(56) References Cited

U.S. PATENT DOCUMENTS

| | | | |
|---|---|---|---|
| 4,542,142 | A | 9/1985 | Martel et al. |
| 2007/0282097 | A1 * | 12/2007 | Ohgi et al. .................... 536/23.1 |

FOREIGN PATENT DOCUMENTS

| | | |
|---|---|---|
| DD | 1 33 885 A1 | 1/1979 |
| EP | 1 795 536 A1 | 6/2007 |
| GB | 2016273 A | 9/1979 |
| JP | 2010-265304 * | 11/2010 |
| WO | 2004/085494 A1 | 10/2004 |
| WO | 2005/023828 A1 | 3/2005 |
| WO | 2005/092909 A1 | 10/2005 |
| WO | 2006/022323 A1 | 3/2006 |
| WO | 2007/064291 A1 | 6/2007 |

OTHER PUBLICATIONS

Machine translation of JP 2010-265304 (2010) [online] [Retrieved Oct. 15, 2012] Retrieved from the internet <http://dossier1.ipdl.inpit.go.jp/AIPN/odse_top_dn.ipdl?N0000=7400>.*

International Preliminary Report on Patentability issued with respect to counterpart International Application No. PCT/JP2010/065900, dated Mar. 29, 2012.

English translation of International Preliminary Report on Patentability issued with respect to counterpart International Application No. PCT/JP2010/065900, dated Apr. 19, 2012.

N. Usman et al., "Automated Chemical Synthesis of Long Oligoribonucleotides Using 2'-O-Silylated Ribonucleoside 3'-O-Phosphoramidites on a Controlled-Pore Glass Support . . . ", J. Am. Chem. Soc., vol. 109, No. 25, 1987, Nov. 26, 1986, pp. 7845-7854.

Tadashi Umemoto et al., "Oligoribonucleotide Synthesis by the use of 1-(2-cyanoethoxy)ethyl (CEE) as a 2'-hydroxy protecting group.", Tetrahedron Letters 45 (2004) Science@Direct www.sciencedirect.com, Oct. 22, 2004, pp. 9529-9531.

James H. Clark, "Fluoride Ion as a Base in Organic Synthesis", Chemicals Reviews. vol. 80, No. 5 1980 American Chemical Society, Jul. 8, 1980, pp. 429-452.

Susumu Misaki et al., "Dehydration of 2-Trifluoromethyl-3,3,3-Trifluoropropanol with Base.", Journal of Fluorine Chemistry, 24 (1984)., Sep. 24, 1983, pp. 531-533.

Stefan Matysiak et al., "Acetals as New 2'-O-Protecting Functions for the Synthesis of the Oligoribonucleotides: Synthesis of Uridine Building Blocks and Evaluation of Their Relative Acid Stability.", Helvetica Chimica ACTA—vol. 81 1998, May 11, 1998, pp. 1545-1566.

International Search Report and Written Opinion from PCT/JP2010/065900, filed Sep. 15, 2010.

European Search Report issued with respect to counterpart European Application No. 10817185.1, dated Apr. 8, 2013.

* cited by examiner

Primary Examiner — Scarlett Goon
(74) Attorney, Agent, or Firm — Greenblum & Bernstein, P.L.C.

(57) ABSTRACT

A protective group represented by the following general formula (I) (the oxygen atom attached with * represents oxygen atom of 2'-hydroxyl group of a ribonucleoside, a ribonucleotide or a derivative thereof; $R^1$ and $R^2$ both represent hydrogen atom, or represent a halogen atom, a $C_{1-6}$ alkyl group, or a $C_{1-6}$ halo-substituted alkyl group; $R^3$ and $R^4$ represent hydrogen atom, a halogen atom, a $C_{1-6}$ alkyl group, or a $C_{1-6}$ halo-substituted alkyl group; and $R^5$ and $R^6$ represent a halogen atom, a $C_{1-6}$ halo-substituted alkyl group, cyano group, nitro group, or the like), which is stable under the reaction conditions of the nucleic acid synthetic cycles and has little steric hindrance, and can be removed under mild conditions using fluoride ions as a base.

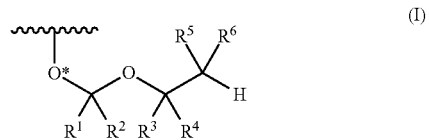

(I)

14 Claims, No Drawings

PROTECTIVE GROUP FOR SYNTHESIS OF RNA AND DERIVATIVE

This application claims the benefit of Provisional Application No. 61/242,877, filed Sep. 16, 2009.

TECHNICAL FIELD

The present invention relates to a novel protective group that can be used in chemical synthesis of oligoribonucleic acids, and the like.

BACKGROUND ART

Oligoribonucleic acids have variety of usefulness such as applicability as active ingredients of medicaments for controlling expression of genes including antisense RNA and RNAi, as well as applicability as RNA probes for gene analyses. Oligoribonucleic acids can generally be prepared by the solid-phase synthetic method using a phosphoroamidite compound (J. Am. Chem. Soc., 109, 7845, 1987). However, since β-D-ribose of ribonucleotide constituting ribonucleic acid has hydroxyl group at the 2-position (in the specification, this hydroxyl group is referred to as "2'-hydroxyl group" for ribonucleotides and derivatives thereof, as well as for ribonucleosides and derivatives thereof), production of oligoribonucleic acids based on the solid phase synthetic method has a problem that production yield is significantly influenced by type of protective group for this 2'-hydroxyl group, unlike the methods for producing deoxyribonucleic acids (DNA).

As protective groups of the 2'-hydroxyl group used for the oligoribonucleic acid preparation, there are known silyl type protective groups such as tert-butyldimethylsilyl (TBDMS) group and triisopropylsilyl (TIPS) group described in the aforementioned publication (J. Am. Chem. Soc., 109, 7845, 1987). In particular, since TBDMS can be removed by treatment with fluoride ions under neutral conditions, the protective group has been widely used in preparation of oligoribonucleic acids. However, when TBDMS is used as a protective group of the 2'-hydroxyl group, TBDMS may translocates to a 3'-hydroxyl group at the time of phosphoroamidation of the 3'-hydroxyl group. Moreover, since the TBDMS group is three-dimensionally bulky, the group also has a problem of reduced efficiency of condensation reaction for generating a nucleotide bond due to steric hindrance.

It is also known that use of 1-(2-cyanoethoxy)ethyl (CEE) group provided as an acetal type protective group (Helvetica Chimica Acta, 81, 1545, 1998; Tetrahedron Lett., 45, 9529, 2004) as a protective group of the 2'-hydroxyl group achieves efficient preparation of oligoribonucleic acids (International Patent Publication WO2005/23828). However, it is also known that an acetal type protective group is generally unstable to acids, thus sufficient stability cannot be secured for long chain synthesis, and acrylonitrile produced in the reaction system at the time of deprotection causes a side reaction with the nucleobase moieties. Moreover, since this protective group has an asymmetric center, the group also has a problem that a reaction product becomes a mixture of diastereomers after the introduction of the protective group, and thus identification of the target compound becomes difficult.

In order to solve the above problems, a protective group represented by —CH$_2$—O—CH$_2$—CH$_2$-WG$^1$ has been proposed as a protective group of the 2'-hydroxyl group used in the preparation of oligoribonucleic acids (International Patent Publication WO2006/22323, WG$^1$ in the formula represents an electron withdrawing group), and a protective group using cyano group as the electron withdrawing group represented by WG$^1$ (—CH$_2$—O—CH$_2$—CH$_2$—CN, this protective group may also be referred to as "CEM") is specifically disclosed in the aforementioned publication. This protective group has characteristic features that the group has little steric hindrance, and can be removed by treatment with fluoride ion under neutral conditions. However, this protective group also has a problem that removal efficiency at the time of treatment with fluoride ions is not fully satisfactory, and strict control of water content in a solvent used for the process of removing the protective group is required, which is undesirable from a viewpoint of manufacturing cost. Furthermore, as in the case of the CEE group, it is known that acrylonitrile is generated in the reaction system at the time of deprotection to cause a side reaction with the nucleobase moieties, and therefore, addition of a scavenger to the reaction system is essential, which causes problems from viewpoints of manufacturing cost and load on the environment.

PRIOR ART REFERENCES

Patent Documents

Patent document 1: International Patent Publication WO2006/22323
Patent document 2: International Patent Publication WO2005/23828

Non-Patent Documents

Non-patent document 1: J. Am. Chem. Soc., 109, 7845, 1987
Non-patent document 2: Helvetica Chimica Acta, 81, 1545, 1998
Non-patent document 3: Tetrahedron Lett., 45, 9529, 2004

SUMMARY OF THE INVENTION

Object to be Achieved by the Invention

An object of the present invention is to provide a protective group for the 2'-hydroxyl group of a ribonucleoside, a ribonucleotide or a derivative thereof used for the production of oligoribonucleic acids and the like.

More specifically, the object of the present invention is to provide a protective group as mentioned above which is stable under the reaction conditions of the nucleic acid synthesis cycle, and has little steric hindrance, and which is removable under mild conditions using fluoride ions as a base (Chem. Rev., 80, 429, 1980), or removable in the presence of a nucleophile scavenger such as a silylating reagent, or under strongly basic conditions.

Means for Achieving the Object

The inventors of the present invention conducted various researches to achieve the aforementioned object, and as a result, they found that a protective group represented by the following general formula (I) had superior properties that the group was stable under the reaction conditions of the nucleic acid synthesis cycle and the group had little steric hindrance, and that the group was very efficiently and quickly removable by treatment with fluoride ions under mild conditions, and was easily removable even in the presence of water, which allows the use of a usually available solvent, per se, in the deprotection process without any particular consideration on moisture content of the solvent. Furthermore, they also found that the group was quickly removable even under strongly basic conditions in the presence of a nucleophile scavenger such as a silylating reagent. The present invention was accomplished on the basis of the aforementioned findings.

The present invention thus provides a protective group for 2'-hydroxyl group of a ribonucleoside, a ribonucleotide, or a derivative thereof, which is represented by the following general formula (I):

[Formula 1]

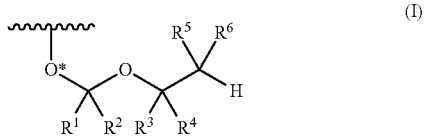

(in the formula, the oxygen atom attached with * represents oxygen atom of 2'-hydroxyl group of a ribonucleoside, a ribonucleotide, or a derivative thereof, $R^1$ and $R^2$ both represent hydrogen atom, or independently represent a halogen atom, a $C_{1-6}$ alkyl group, or a $C_{1-6}$ halo-substituted alkyl group; $R^3$ and $R^4$ independently represent hydrogen atom, a halogen atom, a $C_{1-6}$ alkyl group, or a $C_{1-6}$ halo-substituted alkyl group; and $R^5$ and $R^6$ independently represent a halogen atom, a $C_{1-6}$ halo-substituted alkyl group, cyano group, or nitro group, or $R^5$ and $R^6$ bind to each other to represent a 9-fluorenyl group which may be substituted with a fluorine atom). As the halogen atom, fluorine atom is preferred, and as the halo-substituted alkyl group, a fluoroalkyl group is preferred.

According to preferred embodiments of the aforementioned invention, there are provided the aforementioned protective group, wherein $R^1$ and $R^2$ represent hydrogen atom; the aforementioned protective group, wherein $R^3$ and $R^4$ represents hydrogen atom or fluorine atom; the aforementioned protective group, wherein both $R^3$ and $R^4$ represent hydrogen atom; the aforementioned protective group, wherein $R^5$ and $R^6$ represent the same substituent selected from a fluoro-substituted $C_{1-6}$ alkyl group, cyano group and nitro group; the aforementioned protective group, wherein $R^5$ and $R^6$ represent the same substituent selected from a fluoro-substituted $C_{1-6}$ alkyl group and cyano group; the aforementioned protective group, wherein $R^5$ and $R^6$ represent the same fluoro-substituted $C_{1-6}$ alkyl group; the aforementioned protective group, wherein $R^5$ and $R^6$ represent the same perfluoro($C_{1-6}$ alkyl) group; and the aforementioned protective group, wherein both $R^5$ and $R^6$ represent trifluoromethyl group.

According to a preferred embodiment of the aforementioned invention, there is also provided the aforementioned protective group, wherein the derivative of a ribonucleotide is a phosphoroamidite compound.

From another aspect of the present invention, there is provided a ribonucleoside, a ribonucleotide, or a derivative thereof, wherein oxygen atom of 2'-hydroxyl group is protected with the aforementioned protective group.

Preferred examples of the derivative of ribonucleotide include a phosphoroamidite compound, and as a particularly preferred phosphoroamidite compound protected with the aforementioned protective group, the present invention also provides a compound represented by the following general formula (II);

[Formula 2]

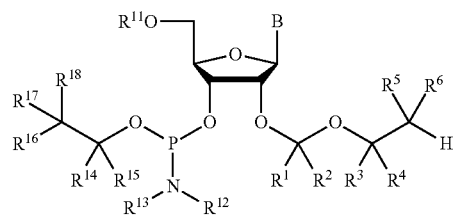

(in the formula, B represents a natural or non-natural nucleobase which may have a protective group; $R^1$, $R^2$, $R^3$, $R^4$, $R^5$, and $R^6$ have the same meanings as those defined above; $R^{11}$ represents a trityl group which may have a substituent (two phenyl groups among three phenyl groups constituting the trityl group may bind to each other via oxygen atom to form a xanthene ring); $R^{12}$ and $R^{13}$ independently represent a $C_{1-6}$ alkyl group, or $R^{12}$ and $R^{13}$ may bind to each other to form a saturated 5- or 6-membered ring (this ring may have one or two or more oxygen atoms or sulfur atoms as ring-constituting atoms); $R^{14}$ and $R^{15}$ independently represent hydrogen atom or a $C_{1-6}$ alkyl group, provided that $R^{14}$ may bind to $R^{13}$ to form a 5- or 6-membered ring; $R^{16}$ represents an electron withdrawing group, or when $R^{14}$ binds to $R^{13}$ to form a 5- or 6-membered ring, $R^{16}$ represents an electron withdrawing group or hydrogen atom, and $R^{17}$ and $R^{18}$ represent hydrogen atom or a $C_{1-6}$ alkyl group, or $R^{16}$, $R^{17}$, and $R^{18}$ bind to one another to represent an aryl group together with the carbon atom to which they bind).

As still further aspects, the present invention provides a method for preparing an oligoribonucleic acid by using the aforementioned phosphoroamidite compound, and an oligoribonucleic acid prepared by the above preparation method. The present invention also provides an oligoribonucleic acid immobilized on a solid phase and having the aforementioned protective group, which is obtained as a synthetic intermediate in the preparation method.

The present invention also provides a reagent for protecting 2'-hydroxyl group of a ribonucleoside, a ribonucleotide, or a derivative thereof, which comprises a compound represented by the following general formula

[Formula 3]

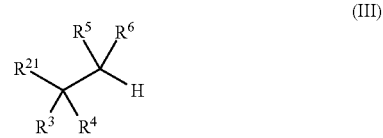

[in the formula, $R^3$, $R^4$, $R^5$, and $R^6$ have the same meanings as those defined above, $R^{21}$ represents hydroxyl group, $R^{22}$—S—C($R^1$)($R^2$)—O— (in the formula, $R^{22}$ represent a $C_{1-6}$ alkyl group, and $R^1$ and $R^2$ have the same meanings as those defined above), or X—C($R^1$)($R^2$)—O— (in the formula, X represents a leaving group, and $R^1$ and $R^2$ have the same meanings as those defined above)]. Preferred examples of the leaving group include chlorine atom, bromine atom, an alkylsulfonyl group such as methanesulfonyl group, an arylsulfonyl group such as p-toluenesulfonyl group, and the like.

There is further provided a method for protecting the 2'-hydroxyl group of a ribonucleoside, a ribonucleotide, or a derivative thereof by using the reagent represented by the aforementioned general formula (III), which comprises the step of reacting the reagent represented by the aforementioned general formula (III) and a ribonucleoside, a ribonucleotide, or a derivative thereof of which 2'-hydroxyl group is protected with a $C_{1-6}$ alkylthiomethyl group.

Effect of the Invention

The protective group represented by the aforementioned general formula (I) is stable under the reaction conditions of the nucleic acid synthetic cycle and having little steric hindrance, and can be very efficiently removed in a short time by, for example, a treatment with a fluorine compound under mild conditions. Therefore, the group has ideal properties as a protective group for the 2'-hydroxyl group of a ribonucleoside, a ribonucleotide, or a derivative thereof. The aforementioned protective group also has a superior property that the group can be easily removed even in the presence of water, and an ordinarily available solvent without any treatment can be used for the deprotection step particularly regardless of moisture content of the solvent. Therefore, the group has a desirable property from a viewpoint of saving manufacturing cost. Furthermore, the group can be quickly removed even under strongly basic conditions in the presence of a nucleophile scavenger such as a silylating reagent, and therefore, the group also has an advantage that the group will allow multiple step deprotection as used in conventional methods unnecessary by appropriately choosing combination of protective groups.

MODES FOR CARRYING OUT THE INVENTION

The oxygen atom attached with * in the aforementioned general formula (I) represents oxygen atom of the 2'-hydroxyl group of a ribonucleoside, a ribonucleotide, or a derivative thereof.

In the specification, the base constituting the ribonucleoside, ribonucleotide, or derivative thereof is not particularly limited, and an any natural or non-natural base can be used. For example, pyrimidine bases such as cytosine and uracil, and purine bases such as adenine and guanine can be used. As the base, modified bases such as 5-methylcytosine, 5-hydroxymethylcytosine, 5-fluorouracil, 5-methyluracil, 2-thiouracil, 6-azauracil, 5-hydroxyuracil, 2,6-diaminopurine, 8-azaadenine, 8-azaguanine and isoguanine can also be used.

The aforementioned bases may have one or two or more arbitrary substituents. Types, number, and substituting positions of the substituents are not particularly limited, and when two or more substituents exist, they may be the same or different. Examples of the substituents include, for example, a halogen atom, oxo group, thioxo group, nitro group, nitroso group, cyano group, isocyano group, cyanato group, tiocyanato group, isocyanato group, isothiocyanato group, hydroxy group, sulfanyl group, carboxy group, sulfanylcarbonyl group, oxalo group, mesoxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, a $C_1$ to $C_6$ alkyl group, a $C_2$ to $C_6$ alkenyl group (for example, vinyl group, allyl group, 1-propenyl group, and the like), a $C_2$ to $C_6$ alkynyl group (for example, ethynyl group, 1-propynyl group, and the like), a $C_1$ to $C_6$ alkylidene group, a $C_6$ to $C_{10}$ aryl group, a $C_7$ to $C_{12}$ aralkyl group (for example, benzyl group, phenethyl group, 1-naphthylmethyl group, 2-naphthylmethyl group, and the like), a $C_7$ to $C_{12}$ aralkylidene group (for example, benzylidene group, phenethylidene group, 1-naphthylmethylidene group, 2-naphthylmethylidene group, and the like), a $C_1$ to $C_6$ alkoxy group, a $C_6$ to $C_{10}$ aryloxy group (for example, phenoxy group, 1-naphthyloxy group, 2-naphthyloxy group, and the like), a $C_7$ to $C_{12}$ aralkyloxy group (for example, benzyloxy group, (1-naphthylmethyl)oxy group, (2-naphthylmethyl)oxy group, and the like), a $C_1$ to $C_6$ alkylsulfanyl group (for example, methylsulfanyl group, ethylsulfanyl group, and the like), a $C_6$ to $C_{10}$ arylsulfanyl group (for example, phenylsulfanyl group, 1-naphthylsulfanyl group, 2-naphthylsulfanyl group, and the like), a $C_7$ to $C_{12}$ aralkyloxysulfanyl group (for example, benzylsulfanyl group, (1-naphthylmethyl)sulfanyl group, (2-naphthylmethyl)sulfanyl group, and the like), a $C_1$ to $C_6$ alkanoyl group (for example, acetyl group, propionyl group, n-butyryl group, pivaloyl group, and the like), a $C_6$ to $C_{10}$ aroyl group (for example, benzoyl group, 1-naphthoyl group, 2-naphthoyl group, and the like), a $C_1$ to $C_6$ alkylsulfonyl group (for example, methanesulfonyl group, ethanesulfonyl group, propanesulfonyl group, and the like), a $C_6$ to $C_{10}$ arylsulfonyl group (for example, benzenesulfonyl group, 1-naphthalenesulfonyl group, 2-naphthalenesulfonyl group, and the like), a $C_1$ to $C_6$ alkoxycarbonyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminoxy group, diazo group, semicarbazino group, semicarbazono group, allophanyl group, hydantoyl group, phosphano group, phosphoroso group, phospho group, boryl group, silyl group, stannyl group, selanyl group, oxido group, a heteroaryl group, a partially or completely saturated heterocyclic group consisting of a heteroaryl group a part or all of which double bonds are replaced with single bonds, and the like, but the substituents are not limited to these examples.

The substituents exemplified above may further be substituted with one or two or more kinds of other substituents. Examples of such substituents include, for example, a $C_1$ to $C_6$ halogenated alkyl group (for example, chloromethyl group, dichloromethyl group, trichloromethyl group, difluoromethyl group, trifluoromethyl group, 2,2,2-trifluoroethyl group, pentafluoroethyl group, and the like), a $C_1$ to $C_6$ halogenated alkoxy group (for example, trifluoromethoxy group, pentafluoroethoxy group, and the like), a carboxy-substituted $C_1$ to $C_6$ alkyl group (for example, carboxymethyl group, carboxyethyl group, and the like), a $C_1$ to $C_6$ alkyl-substituted amino group (for example, methylamino group, ethylamino group, and the like), and the like, but the substituents are not limited to these examples.

As the ribonucleoside, a compound consisting of D-ribose to which the aforementioned base bonds, preferably cytidine, uridine, adenosine, guanosine or the like, can be used, and as the ribonucleotide, a compound consisting of a ribonucleoside to which phosphoric acid bonds at the 3'-position via an ester bond, preferably cytidine 3'-phosphate, uridine 3'-phosphate, adenosine 3'-phosphate, guanosine 3'-phosphate and the like, can be used. Examples of the derivative of ribonucleoside include, for example, a protected ribonucleoside, and the like, and examples of the derivative of ribonucleotide include, for example, protected ribonucleotide, an oligonucleotide (for example, those containing about 2 to 100 nucleotide units), a reactive ribonucleotide compound used for synthesis of oligonucleotides (for example, phosphoroamidite compounds used in the solid phase synthesis, and the like), various kinds of production intermediates used in synthesis of oligonucleotides (for example, a nucleotide compound or oligonucleotide compound immobilized on a solid phase and protected with one or more protective groups), and the like, but the derivatives are not limited to these examples. Further, the derivative of ribonucleoside or ribonucleotide may be, for example, a compound having one or two or more arbitrary substituents selected from those explained for the aforementioned base. Types, number, and substituting positions of the substituents are not particularly limited, and when two or more substituents exist, they may be the same or different.

When the ribonucleoside or ribonucleotide has a protective group, it is meant that the compound has one or two or more arbitrary protective groups other than the protective group represented by the aforementioned general formula (I), and these protective groups are used as protective groups for groups other than the 2'-hydroxyl group. Examples of the protective group usable in a ribonucleoside or ribonucleotide include, for example, protective groups for amino group, hydroxyl group, and the like. A for these protective groups, publications such as Green et al., Protective Groups in Organic Synthesis, 3rd Edition, 1999, John Wiley & Sons, Inc. can be referred to.

In the general formula (I), both $R^1$ and $R^2$ are hydrogen atoms, or they independently represent a halogen atom, a $C_{1-6}$ alkyl group, or a halo-substituted $C_{1-6}$ alkyl group. In the specification, the alkyl group or an alkyl moiety of a substituent having the alkyl moiety (for example, alkyl moiety of the fluoro-substituted $C_{1-6}$ alkyl group) may be any of linear, branched and cyclic alkyl groups and an alkyl group consisting of a combination thereof. In the specification, the halogen atom may be any of fluorine atom, chlorine atom, bromine atom, and iodine atom. Fluorine atom can be preferably used as the halogen atom represented by $R^1$ or $R^2$. As the halo-substituted $C_{1-6}$ alkyl group represented by $R^1$ or $R^2$, a fluoro-substituted $C_{1-6}$ alkyl group can be preferably used. As the fluoro-substituted $C_{1-6}$ alkyl group, a $C_{1-6}$ alkyl group having one or two or more fluorine atoms at arbitrary positions can be used, a perfluoroalkyl group can be preferably used, and trifluoromethyl group, pentafluoroethyl group, and the like can be more preferably used. It is preferred that both $R^1$ and $R^2$ are hydrogen atoms, when both $R^1$ and $R^2$ are halo-substituted $C_{1-6}$ alkyl groups. It is also preferred that $R^1$ and $R^2$ are the same fluoro-substituted $C_{1-6}$ alkyl groups, for example, trifluoromethyl groups. It is most preferred that both $R^1$ and $R^2$ are hydrogen atoms.

$R^3$ and $R^4$ independently represent hydrogen atom, a halogen atom, a $C_{1-6}$ alkyl group, or a halo-substituted $C_{1-6}$ alkyl group. As the halogen atom represented by $R^3$ or $R^4$, fluorine atom is preferred. As the halo-substituted $C_{1-6}$ alkyl group represented by $R^3$ or $R^4$, a fluoro-substituted $C_{1-6}$ alkyl group can be preferably used. As the $C_{1-6}$ fluoro-substituted alkyl group, a $C_{1-6}$ alkyl group having one or two or more fluorine atoms at arbitrary positions can be used, a perfluoroalkyl group can be preferably used, and trifluoromethyl group, pentafluoroethyl group, and the like can be more preferably used. It is preferred that both $R^3$ and $R^4$ are hydrogen atoms. When both $R^3$ and $R^4$ are halo-substituted $C_{1-6}$ alkyl groups, it is also preferred that $R^3$ and $R^4$ are the same fluoro-substituted $C_{1-6}$ alkyl groups, for example, trifluoromethyl groups. It is most preferred that both $R^3$ and $R^4$ are hydrogen atoms.

$R^5$ and $R^6$ independently represent a halogen atom, a halo-substituted $C_{1-6}$ alkyl group, cyano group, or nitro group. As the halogen atom represented by $R^5$ or $R^6$, fluorine atom is preferred. As the halo-substituted $C_{1-6}$ alkyl group represented by $R^5$ or $R^6$, a fluoro-substituted $C_{1-6}$ alkyl group can be preferably used. As the fluoro-substituted $C_{1-6}$ alkyl group, a $C_{1-6}$ alkyl group having one or two or more fluorine atoms at arbitrary positions can be used. A perfluoroalkyl group can be preferably used, and trifluoromethyl group, pentafluoroethyl group, and the like can be more preferably used. $R^5$ and $R^6$ also bind to each other to represent 9-fluorenyl group, and the 9-fluorenyl group may have one or more fluorine atoms at arbitrary positions. It is preferred that $R^5$ and $R^6$ are the same fluoro-substituted $C_{1-6}$ alkyl groups, more preferably the same perfluoro($C_{1-6}$ alkyl) groups, for example, trifluoromethyl groups or pentafluoroethyl groups, and it is also preferred that both $R^5$ and $R^6$ are cyano groups or nitro groups. It is particularly preferred that $R^5$ and $R^6$ are the same perfluoro ($C_{1-6}$ alkyl) groups, for example, trifluoromethyl groups or pentafluoroethyl groups, and it is most preferred that both $R^5$ and $R^6$ are trifluoromethyl groups. The protective group having the same perfluoro($C_{1-6}$ alkyl) groups as $R^5$ and $R^6$ imparts fluorous properties to the protected compound to make separation and purification of the product easier, and therefore it is advantageous from an industrial viewpoint.

Examples of preferred embodiments of the protective group represented by general formula (I) include the protective group in which both $R^1$ and $R^2$ are hydrogen atoms, both $R^3$ and $R^4$ are hydrogen atoms, and $R^5$ and $R^6$ are the same fluoro-substituted $C_{1-6}$ alkyl groups, examples of more preferred embodiments thereof include the protective group in which both $R^1$ and $R^2$ are hydrogen atoms, both $R^3$ and W are hydrogen atoms, and $R^5$ and $R^6$ are the same perfluoro($C_{1-6}$ alkyl) groups, and examples of particularly preferred embodiments thereof include the protective group in which both $R^1$ and $R^2$ are hydrogen atoms, both $R^3$ and $R^4$ are hydrogen atoms, and both $R^5$ and $R^6$ are trifluoromethyl groups. However, the protective group of the present invention is not limited to the aforementioned specific embodiments. The protective groups of the aforementioned embodiments do not have an asymmetric carbon. Accordingly, a reaction product after being introduced with the above groups is not obtained as a mixture of diastereomers, and therefore, they are also advantageous from a viewpoint of easy identification of a target compound.

Although a means for introducing the protective group represented by the aforementioned general formula (I) into the 2'-hydroxyl group of a ribonucleoside, a ribonucleotide, or a derivative thereof is not particularly limited, it is usually desirable to protect any reactive functional groups other than the 2'-hydroxyl group with arbitrary protective groups in advance of the reaction. Such protective groups can be appropriately chosen and introduced by referring to publications, for example, Green et al., Protective Groups in Organic Synthesis, 3rd Edition, 1999, John Wiley & Sons, Inc., and the like.

When a compound represented by the aforementioned general formula (III) wherein $R^{21}$ is hydroxyl group is used, the aforementioned protective group can generally be easily introduced by reacting the compound represented by the aforementioned general formula (III) with a ribonucleoside, a ribonucleotide, or a derivative thereof of which 2'-hydroxyl group is protected with a $C_{1-6}$ alkylthiomethyl group. The aforementioned reaction can be performed under anhydrous conditions in the presence of an oxidizing agent such as an acid or N-iodosuccinimide (NIS). For example, the reaction can be performed in the presence of an aprotic solvent, for example, an ether type solvent such as tetrahydrofuran (THF), and molecular sieves (MS) as a dehydrating agent. As the acid, for example, an acid such as trimethylsilyl trifluoromethanesulfonate can be used. In the aforementioned reaction, the sulfur atom of the alkylthio group in the thioketal group is iodinated, and then a ketal compound in which the protective group represented by the aforementioned general formula (I) is introduced is generated by replacement with the hydroxyl group of the alcohol compound represented by the aforementioned general formula (III). The reaction can be performed, for example, by using molecular sieves 4A or the like at a reaction temperature of about −50 to −40° C. However, is should be understood that the reaction conditions for introduction of the protective group represented by general formula (I) are not limited to those specified above, and can be appropriately chosen by those skilled in the art.

Further, when a compound represented by the aforementioned general formula (III) in which $R^{21}$ is not hydroxyl group is used, the reaction can be performed as an ordinary substitution reaction. In the case of the compound wherein $R^{21}$ is the group represented as $R^{22}$—S—$C(R^1)(R^2)$—O—, the reaction can be performed in an aprotic solvent such as tetrahydrofuran in the presence of molecular sieves, trifluoromethanesulfonic acid, N-iodosuccinimide, or the like, and in the case of the compound wherein $R^{21}$ is a group represented as $X—C(R^1)(R^2)—O—$, the reaction can be performed in an aprotic solvent such as 1,2-dichloroethane in the presence of dibutyltin dichloride, diisopropylethylamine, or the like. However, the reaction conditions are not limited to these conditions.

A typical example of the reaction process using a compound represented by the aforementioned general formula (III) in which $R^{21}$ is hydroxyl group is shown below. However, the scope of the present invention is not limited to the method shown in the following scheme. In the scheme, Me represents methyl group, Et represents ethyl group, DIBAL represents diisobutylaluminum hydride, Ur represents a uracil base, TMSOTf represents trimethylsilyl trifluoromethanesulfonate, MS4A represents molecular sieves 4A, THF represents tetrahydrofuran, and MS represents N-iodosuccinimide. Further, a specific method for preparing the compound (I) mentioned in the scheme is shown in the examples.

[Formula 4]

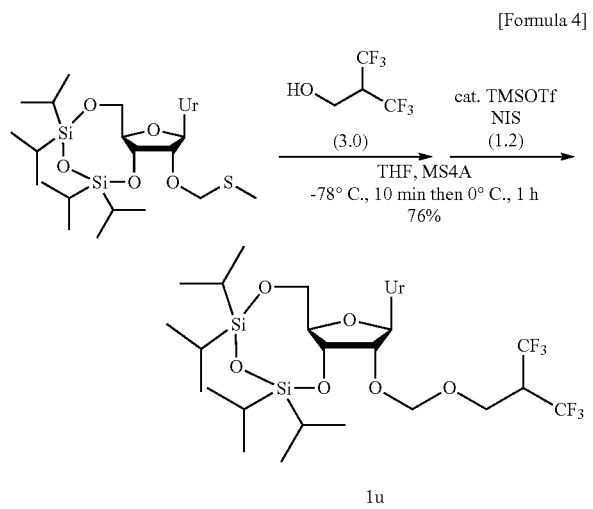

Preferred examples of a ribonucleotide derivative having the protective group represented by the general formula (I) include a phosphoroamidite compound represented by the aforementioned general formula (II). In the general formula (II), B represents the nucleobase explained above, and $R^1$, $R^2$, $R^3$, $R^4$, $R^5$, and $R^6$ have the same meanings as those explained above. $R^{11}$ represents a trityl group which may have a substituent. Examples of the trityl group having a substituent include a trityl group in which one or more phenyl groups constituting the trityl group, preferably two or more such phenyl groups, each have an alkoxy group such as methoxy group at the para-position. However, the present invention is not limited to the above specific embodiment. Further, two of the three phenyl groups constituting the trityl group may bind to each other via oxygen atom to form a xanthene ring. An example of such a case is that the trityl group forms 9-phenylxanthen-9-yl group (pixyl group), and use of pixyl group constitutes a preferred embodiment.

$R^{12}$ and $R^{13}$ independently represent a $C_{1-6}$ alkyl group. Further, $R^{12}$ and $R^{13}$ may bind to each other to form a saturated 5- or 6-membered ring. The ring formed by $R^{12}$, $R^{13}$ and the amino group to which they bind may have one or two or more oxygen atoms or sulfur atoms as ring-constituting atoms. Examples of the saturated ring system to be formed include, for example, pyrrolidin-1-yl, piperidin-1-yl, morpholin-1-yl, thiomorpholin-1-yl and the like, but the ring systems are not limited to these examples.

$R^{14}$ and $R^{15}$ independently represent hydrogen atom or a $C_{1-6}$ alkyl group, and it is preferred that they represent hydrogen atom. $R^{13}$ and $R^{14}$ may bind to each other to form a 5- or 6-membered ring. Even when $R^{12}$ and $R^{13}$ bind to each other to form a saturated 5- or 6-membered ring, $R^{13}$ and $R^{14}$ may bind together to form a 5- or 6-membered ring, and as a result, to form a bicyclic group containing the ring formed by $R^{12}$ and $R^{13}$ and the ring formed by $R^{13}$ and $R^{14}$.

Examples of the electron withdrawing group represented by $R^{16}$ include, for example, cyano group, nitro group, an alkylsulfonyl group, a halogen atom, and a fluoro-substituted $C_{1-6}$ alkyl group (for example, a perfluoro($C_{1-6}$ alkyl) group such as trifluoromethyl group and the like), but the groups are not limited to these examples. Cyano group can be preferably used as $R^{16}$. When $R^{13}$ and $R^{14}$ bind together to form a 5- or 6-membered ring, $R^{16}$ represents an electron withdrawing group or hydrogen atom, preferably a hydrogen atom. $R^{17}$ and $R^{18}$ represent hydrogen atom or a $C_{1-6}$ alkyl group, and it is preferred that both represent hydrogen atom.

Further, it is also preferred that $R^{16}$, $R^{17}$ and $R^{18}$ bind to one another to form an aryl group together with the carbon atom to which they bind. The aryl group may be a substituted or unsubstituted phenyl group, or the like, and the substituted phenyl group may be, for example, a halogenated phenyl group, a nitrophenyl group, trifluoromethylphenyl group, or the like, but the groups not limited to these examples. The aryl group is preferably unsubstituted phenyl group.

The phosphoroamidite compounds of the present invention include arbitrary stereoisomers (optical isomers, diastereoisomers, and the like) in pure forms or not pure forms, arbitrary mixtures of stereoisomers, and the like. Further, when the phosphoroamidite compounds of the present invention form salts, such salts of arbitrary forms are also encompassed within the scope of the present invention. Furthermore, hydrates or solvates of the compounds in free form or in the form of arbitrary salt are also encompassed within the scope of the present invention.

Preferred examples of the phosphoroamidite compound include a compound represented by the following formula (IIA) in which $R^{16}$, $R^{17}$ and $R^{18}$ bind to one another to form phenyl group together with the carbon atom to which they bind. However, the phosphoroamidite compound is not limited to the following compound. The symbols used in the formula have the same meanings as those defined above.

[Formula 5]

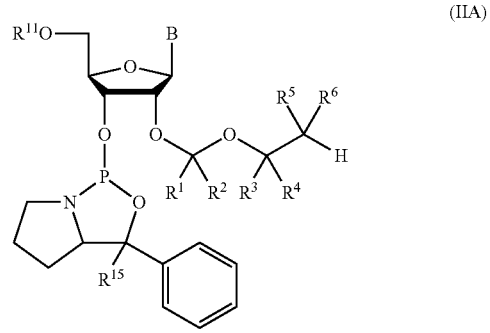

(IIA)

Preferred phosphoroamidite compounds encompassed within the scope of the general formula (IIA) are shown below. However, the compounds represented by the general formula (IIA) are not limited to these examples (in the formulas, Me represents methyl group, and Ph represents phenyl group).

[Formula 6]

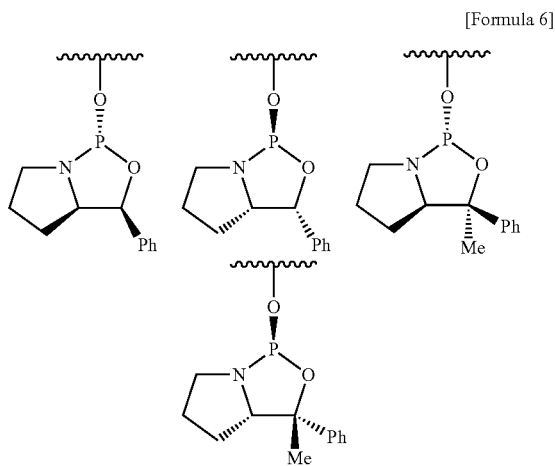

An oligoribonucleic acid can be efficiently produced by using a phosphoroamidite compound represented by the aforementioned general formula (II).

For example, a method for preparing an oligoribonucleic acid by using a phosphoroamidite compound having a protective group represented as —$CH_2$—O—$CH_2$—$CH_2$-$WG^1$ as a protective group for the 2'-position is specifically shown in International Patent Publication WO2006/22323. Preparation of an oligoribonucleic acid using a phosphoroamidite compound represented by the aforementioned general formula (II) can be performed according to the method disclosed in International Patent Publication WO2006/22323 mentioned above. The entire disclosure of International Patent Publication WO2006/22323 mentioned above is herein incorporated by reference as disclosure of this specification. In particular, repetition of processes of the steps A to G and the steps A to D are specifically explained for oligoribonucleic acids represented by the general formula (3) in the paragraphs [0025] to [0033] of the aforementioned international patent publication, and an oligoribonucleic acid can be prepared by using the phosphoroamidite compound of the present invention according to the aforementioned explanation, per se, except for the difference in the protective group of the 2'-hydroxyl group in the phosphoroamidite compound of the present invention. Further, the definitions of the terms used in the above explanation such as "solid phase carrier", "linker" and "acid" are the same as those used in the aforementioned international patent publication.

Further, International Patent Publication WO2005/23828 discloses a method for preparing a ribonucleotide derivative using a ribonucleotide of which 2'-hydroxyl group is protected with 1-(2-cyanoethoxy)ethyl (CEE) group, and various ribonucleotide derivatives can be prepared according to the method disclosed in International Patent Publication WO2005/23828 mentioned above by using a ribonucleotide derivative introduced with the protective group represented by the aforementioned general formula (I). The entire disclosure of International Patent Publication WO2005/23828 mentioned above is herein incorporated by reference as disclosure of this specification.

In addition, in the methods disclosed in these publications, reaction reagents and reaction conditions can be appropriately selected, and appropriate modifications or alterations can be added as required, and it should be understood that these selection, modifications, and alterations can be easily performed by those skilled in the art within routine creative activities.

The protective group represented by the aforementioned general formula (I) can be easily removed by, for example, allowing a fluorine compound such as tetrabutylammonium fluoride to react the group. As a solvent, an aprotic solvent such as tetrahydrofuran, N-methylpyrrolidone, pyridine, and dimethyl sulfoxide, or an arbitrary mixture thereof can be used, but the solvents are not limited to these examples. The fluorine compound can be allowed to react on the protective group in a 100 to 500-fold molar amount on the basis of the protective group to be removed, and the reaction advances at a temperature of about 0 to 80° C., preferably at room temperature, within about several minutes to several hours. Further, for removal of the protective group represented by the aforementioned general formula (I), for example, an organic strong base such as 1,8-diazabicyclo[5.4.0]undec-7-ene (DBU) and concentrated ammonia solution in ethanol can also be used.

Further, for removal of the protective group at the time of synthesis of an oligomer, a means of allowing a strong base to react on the protective group in the presence of a nucleophile scavenger such as a silylating reagent is also effective, in addition to the means of allowing fluoride ions such as tetrabutylammonium fluoride mentioned above to react on the protective group. Examples of the silylating reagent include N,O-bistrimethylsilylacetamide (BSA), N,O-bistrimethylsilyltrifluoroacetamide (BSTFA), chlorotrimethylsilane, 1,1,1,3,3,3-hexamethyldisilazane, and the like, but the reagents are not limited to these examples. Examples of the strong base include, for example, DBU, N-methylpyrrolidine, piperidine, triethylamine, diisopropylethylamine, and the like, but the bases are not limited to these examples. Further, examples of the solvent include an aprotic solvent such as acetonitrile, tetrahydrofuran, and N-methylpyrrolidone, but the solvents are not limited to these examples.

EXAMPLES

The present invention will be more specifically explained with reference to examples. However, the scope of the present invention is not limited to the following examples.

The abbreviations used in the examples are as follows.
ac: acetyl
bz: benzoyl
BFEM: 2-bis(trifluoromethyl)ethoxymethyl
CPG: controlled pore glass
DBU: 1,8-diazabicyclo[5.4.0]undec-7-ene
DCA: dichloroacetic acid
DCM: dichloromethane, $CH_2Cl_2$
DMTr: 4,4'-dimethoxytrityl
HCP: highly cross-linked polystyrene
NIS: N-iodosuccinimide
pac: phenoxyacetyl
TBS: tert-butyldimethylsilyl
TBDPS: tert-butyldiphenylsilyl
TFA: trifluoroacetic acid
TMSOTf: trimethylsilyl trifluoromethanesulfonate
Z-NT: benzyl 3-nitro-1H-1,2,4-triazole-1-carboxylate
Me: methyl
OMe: methoxy

Example 1

(a) 2'-O-(2-Trifluoromethyl-3,3,3-trifluoropropanoxymethyl)-3',5'-O-(1,1,3,3-tetraisopropyldisiloxane-1,3-diyl)uridine (1u)

[Formula 7]

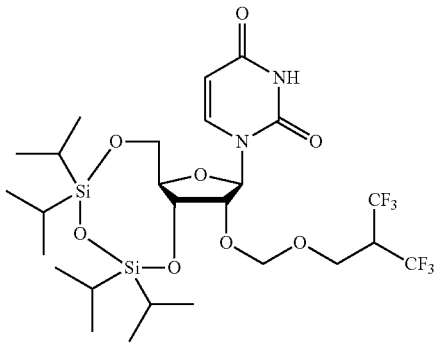

1u

2'-O-Methylthiomethyl-3',5'-O-(1,1,3,3-tetraisopropyldisiloxane-1,3-diyl)uridine (136.7 mg, 250 μmol, Journal of Fluorine Chemistry, 24, pp. 531-533, 1984) was dried by repeated coevaporation with dry toluene, and finally dissolved in tetrahydrofuran (1.5 mL). To the solution, 2-trifluoromethyl-3,3,3-trifluoropropanol (250 μL, 750 μmol) and molecular sieves 4A were added, and the reaction mixture was cooled to −78° C. NIS (67.5 mg, 300 μmmol) and TMSOTf (45 μL, 250 μmmol) were added to the reaction mixture. After stirring over 10 minutes, the mixture was warmed to 0° C., and stirring was continued for 1 hour. Then the reaction was quenched with Et₃N (75 μl). The reaction mixture was diluted with chloroform (25 mL), and washed successively with saturated aqueous Na₂S₂O₃ (25 mL) and saturated aqueous NaHCO₃ (25 mL). The organic layer was dried over Na₂SO₄, filtered to separate Na₂SO₄, and concentrated. The residue was purified by silica gel chromatography (eluent:ethyl acetate:n-hexane=1:5) to give the objective compound 1u (130 mg, 76%) as white foam.

¹H NMR (300 MHz, CDCl₃) δ 9.61 (1H, brs), 7.90 (1H, d, J=8.1 Hz), 5.73 (1H, s), 5.70 (1H, dd, J=8.1, 2.0 Hz), 5.01 (1H, d, J=6.9 Hz), 4.99 (1H, d, J=6.9 Hz), 4.32-4.09 (5H, m), 4.05-3.94 (2H, m), 3.47-3.26 (1H, m), 1.18-0.95 (28H, m)

¹³C NMR (75.5 MHz, CDCl₃) δ 163.7, 150.2, 139.1, 123.1 (2C, q, J=286.1 Hz), 101.8, 94.7, 89.0, 81.7, 78.3, 68.0, 61.3, 59.2, 48.7 (1C, quintet, J=27.9 Hz), 17.4, 17.3, 17.3, 17.2, 16.9, 16.8, 16.8, 16.7, 13.2, 13.1, 12.8, 12.5

MALDI TOF-MS m/z Calcd for C₂₆H₄₂F₆N₂NaO₈Si₂⁺ [M+Na]+ 703.23. found 703.90.

(b) 2'-O-(2-Trifluoromethyl-3,3,3-trifluoropropanoxymethyl)-5'-O-(4,4'-dimethoxytrityl)uridine (2u)

[Formula 8]

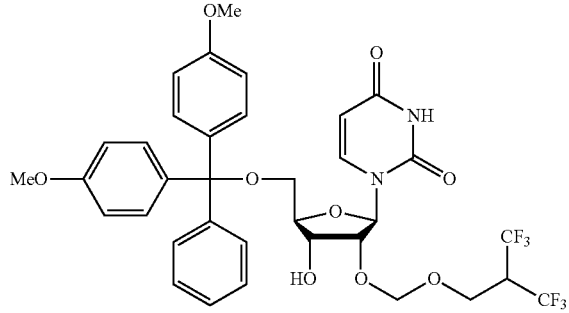

2u

Et₃N.3HF (121 μL, 739 μmol) and Et₃N (53 μL, 380 μmol) were added to a solution of the compound 1u (121 mg, 211 μmol) in dry tetrahydrofuran (2 mL), and the mixture was stirred for 50 minutes at room temperature. The reaction mixture was dried under reduced pressure, the residue was dissolved in a mixed solvent of chloroform and pyridine (10 mL, 1:1, v/v), the solution was washed with water (3×3 mL), and the aqueous layer was back-extracted with chloroform (2×5 mL). The organic layers were combined, dried over Na₂SO₄, and, after Na₂SO₄ was separated by filtration, concentrated to give 2'-O-(2-trifluoromethyl-3,3,3-trifluoropropanoxymethyl)uridine. The crude 2'-O-(2-trifluoromethyl-3,3,3-trifluoropropanoxymethyl)uridine was dried by repeated coevaporation with dry pyridine and dissolved in dry pyridine (2 mL). To the mixture was added DMTr-Cl (78.9 mg, 232 μmol). After the reaction mixture was stirred at room temperature for 15 hours, the reaction was quenched with methanol (500 μL), and the reaction mixture was further stirred for 30 minutes. The solution was dried under reduced pressure, the residue was dissolved in chloroform (5 mL), and washed with 5% aqueous NaHCO₃ (3×5 mL). The aqueous layer was back-extracted with chloroform (3×5 mL), and the combined organic layer was dried over Na₂SO₄, filtered to separate Na₂SO₄, and dried under reduced pressure. The residue was purified by silica gel chromatography (eluent: 0 to 1.5% methanol in dichloromethane) to give the objective compound 2u (118 mg, 90% for 2 steps) as white foam.

¹H NMR (300 MHz, CDCl₃) δ 8.68 (1H, brs), 7.99 (1H, d, J=8.4 Hz), 7.41-7.20 (9H, m), 6.85 (4H, d, J=8.7 Hz), 5.97 (1H, d, J=2.1 Hz), 5.31 (1H, dd, J=8.4, 2.1 Hz), 5.07 (1H, d, J=7.2 Hz), 4.89 (1H, d, J=7.2 Hz), 4.52-4.42 (1H, m), 4.26 (1H, dd, J=5.1, 2.1 Hz), 4.08-3.94 (3H, m), 3.80 (6H, s), 3.61 (1H, dd, J=11.4, 2.1 Hz), 3.53 (1H, dd, J=11.4, 2.7 Hz), 3.28-3.20 (1H, m), 2.31 (1H, d, J=8.1 Hz)

¹³C NMR (75.5 MHz, CDCl₃) δ 162.7, 158.8, 158.8, 150.0, 144.2, 139.8, 135.2, 135.0, 130.2, 130.1, 128.1, 128.1, 127.3, 122.9 (2C, q, J=280.6 Hz), 113.3, 102.3, 95.3, 87.8, 87.3, 80.1, 68.8, 61.8, 61.3, 55.3, 48.9 (1C, quintet, J=27.9 Hz)

MALDI TOF-MS m/z Calcd for C₃₅H₃₄F₆N₂NaO₉⁺ [M+Na]+ 763.21. found 763.73.

(c) 2'-O-(2-Trifluoromethyl-3,3,3-trifluoropropanoxymethyl)-5'-O-(4,4'-dimethoxytrityl)uridine 3'-O-(2-cyanoethyl N,N-diisopropylphosphoramidite) (3u)

[Formula 9]

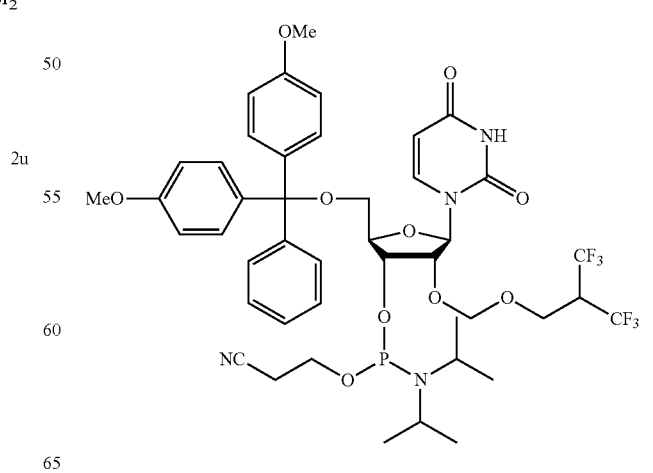

3u

To a solution of the compound 2u (259 mg, 350 μmol) and N,N-diisopropylethylamine (183 μL, 1.05 mmol) in dichlo romethane (3.5 mL), 2-cyanoethyl N,N,-diisopropylchlorophosphoramidite (166 mg, 700 µmol) was added dropwise. The mixture was stirred at room temperature for 1 hour, then diluted with ethyl acetate (35 mL), and washed with a 5% NaHCO$_3$ solution (3×35 mL). The aqueous layer was back-extracted with ethyl acetate (1×30 mL), and the combined organic layer was dried over Na$_2$SO$_4$, filtered to separate Na$_2$SO$_4$, and dried under reduced pressure. The residue was purified by silica gel chromatography (eluent: ethyl acetate: n-hexane=3:7, containing 0.5% pyridine). The fractions containing 3u were collected, and washed with a 5% NaHCO$_3$ solution (3×35 mL). The aqueous layer was back-extracted with ethyl acetate (1×30 mL), and the combined organic layer was dried over Na$_2$SO$_4$, filtered to separate Na$_2$SO$_4$, and dried under reduced pressure to give the objective compound 3u (279 mg, 85%) as white foam.

$^1$H NMR (300 MHz, CDCl$_3$) δ 8.64 (1H, brs), 8.00 (0.5H, d, J=8.4 Hz, diastereomer), 7.96 (0.5H, d, J=8.4 Hz, diastereomer), 7.44-7.21 (9H, m), 6.88-6.80 (4H, m), 6.00 (1H, d, J=2.7 Hz), 5.28 (0.5H, d, J=8.4 Hz, diastereomer), 5.22 (0.5H, d, J=8.4 Hz, diastereomer), 5.00 (0.5H, d, J=6.9 Hz, diastereomer), 4.92 (0.5H, d, J=7.2 Hz, diastereomer), 4.89 (0.5H, d, J=7.2 Hz, diastereomer), 4.87 (0.5H, d, J=6.9 Hz, diastereomer), 4.62-4.50 (1H, m), 4.40-4.34 (1H, m), 4.21 (1H, dd, J=17.7, 6.9 Hz), 4.10 (1H, dt, J=11.0, 4.5 Hz), 4.03-3.23 (8H, m), 3.80 (6H, 2s, diastereomer), 2.63 (1H, t, J=6.0 Hz, diastereomer), 2.43 (1H, t, J=6.2 Hz, diastereomer), 1.22-1.10 (11H, m), 1.02 (3H, d, J=6.9 Hz)

$^{13}$C NMR (75.5 MHz, CDCl$_3$) δ 163.4, 158.7, 150.4, 150.4, 144.2, 144.0, 139.8, 135.1, 135.0, 135.0, 134.8, 130.2, 127.9, 127.9, 127.2, 123.1 (2C, q, J=284.9 Hz), 117.5, 117.3, 113.2, 102.3, 95.1, 94.9, 88.2, 88.0, 87.1, 87.0, 82.4, 82.1, 82.0, 78.4, 78.2, 78.2, 70.6, 70.3, 70.1, 69.9, 61.7, 61.5, 61.0, 61.0, 58.3, 58.0, 57.8, 55.2, 55.2, 48.6 (1C, quintet, J=27.9 Hz), 43.3, 43.2, 43.1, 43.1, 24.6, 24.5, 24.4, 24.3, 20.3, 20.2, 20.1

$^{31}$PNMR (121.5 MHz, CDCl$_3$) δ 152.1 (0.5P, s, diastereomer), 150.8 (0.5P, s, diastereomer)

ESI TOF-MS m/z Calcd for C$_{44}$H$_{52}$F$_6$N$_4$O$_{10}$P$^+$ [M+H]+ 941.33. found 941.45.

Example 2

(a) N$^6$-Acetyl-2'-O-(2-trifluoromethyl-3,3,3-trifluoropropanoxymethyl)-3',5'-O-(1,1,3,3-tetraisopropyldisiloxane-1,3-diyl)adenosine (1a)

[Formula 10]

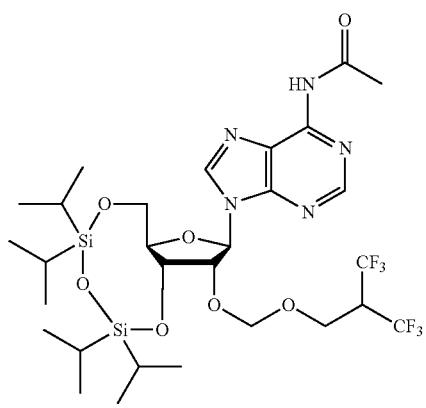

1a

This compound was synthesized in the same manner as that used for the compound 1u by using N$^6$-acetyl-2'-O-methylthiomethyl-3',5'-O-(1,1,3,3-tetraisopropyldisiloxane-1,3-diyl)adenosine instead of 2'-O-methylthiomethyl-3',5'-O-(1,1,3,3-tetraisopropyldisiloxane-1,3-diyl)uridine. Yield was 65% (white foam).

$^1$H NMR (300 MHz, CDCl$_3$) δ 8.63 (1H, s), 8.55 (1H, brs), 8.32 (1H, s), 6.08 (1H, s), 5.10 (1H, d, J=7.2 Hz), 4.96 (1H, d, J=7.2 Hz), 4.67 (1H, dd, J=9.6, 4.5 Hz), 4.48 (1H, d, J=4.5 Hz), 4.34-4.14 (3H, m) 4.08-3.96 (2H, m), 3.53-3.38 (1H, m), 2.62 (3H, s), 1.16-0.92 (28H, m)

$^{13}$C NMR (75.5 MHz, CDCl$_3$) δ 170.4, 152.3, 150.1, 149.2, 140.75, 123.0 (2C, q, J=281.8 Hz), 122.3, 95.0, 88.7, 81.5, 78.1, 69.0, 61.4, 59.5, 49.0 (1C, quintet, J=27.9 Hz), 25.7, 17.4, 17.3, 17.2, 17.0, 16.9, 16.9, 16.8, 13.3, 12.9, 12.8, 12.6

MALDI TOF-MS m/z Calcd for C$_{29}$H$_{45}$F$_6$N$_5$NaO$_7$Si$_2$$^+$ [M+Na]+ 768.27. found 768.81.

(b) N$^6$-Acetyl-2'-O-(2-trifluoromethyl-3,3,3-trifluoropropanoxymethyl)-5'-O-(4,4'-dimethoxytrityl)adenosine (2a)

[Formula 11]

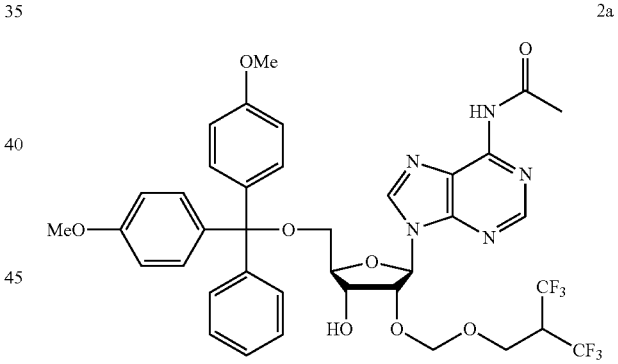

2a

This compound was synthesized in the same manner as that used for the compound 2u by using the compound 1a instead of the compound 1u. Yield was 81% (for 2 steps, white foam).

$^1$H NMR (300 MHz, CDCl$_3$) δ 9.15 (1H, brs), 8.59 (1H, s), 8.24 (1H, s), 7.47-7.15 (9H, m), 6.79 (4H, d, J=8.7 Hz), 6.23 (1H, d, J=4.5 Hz), 4.93 (1H, t, J=4.5 Hz), 4.86 (2H, s), 4.62-4.54 (1H, m), 4.30-4.24 (1H, m), 3.94 (1H, dd, J=11.0, 5.1 Hz), 3.83 (1H, dd, J=11.0, 4.5 Hz), 3.76 (6H, s), 3.55 (1H, dd, J=10.8, 3.0 Hz), 3.45 (1H, dd, J=10.8, 3.9 Hz), 3.26-3.10 (1H, m), 3.08 (1H, d, J=5.4 Hz), 2.59 (3H, s)

$^{13}$C NMR (75.5 MHz, CDCl$_3$) δ 170.5, 158.6, 152.4, 150.8, 149.2, 144.3, 141.4, 135.5, 135.4, 130.0, 128.1, 127.9, 127.7, 127.0, 122.8 (2C, q, J=281.5 Hz), 122.1, 113.2, 95.8, 87.1, 86.8, 84.0, 80.1, 70.4, 62.8, 61.7, 55.2, 48.8 (1C, quintet, J=27.9 Hz), 25.7

MALDI TOF-MS m/z Calcd for $C_{38}H_{37}F_6N_5NaO_8^+$ [M+Na]$^+$ 828.24. found 828.83.

(c) N$^6$-Acetyl-2'-O-(2-trifluoromethyl-3,3,3-trifluoropropanoxymethyl)-5'-O-(4,4'-dimethoxytrityl)adenosine 3'-O-(2-cyanoethyl N,N-diisopropylphosphoramidite) (3a)

[Formula 12]

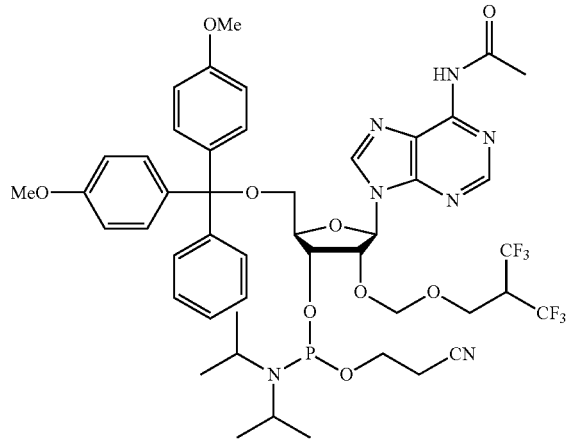

3a

This compound was synthesized in the same manner as that used for the compound 3u by using the compound 2a instead of the compound 2u. Yield was 70% (white foam).

$^1$H NMR (300 MHz, CDCl$_3$) δ 8.83 (1H, brs), 8.59 (1H, s), 8.23 (0.5H, s, diastereomer), 8.23 (0.5H, s, diastereomer), 7.48-7.10 (9H, m), 6.86-6.72 (4H, m), 6.21 (0.5H, d, J=4.8 Hz, diastereomer), 6.17 (0.5H, d, J=5.1 Hz, diastereomer), 5.06-4.62 (4H, m), 4.44-4.30 (1H, m), 3.86-3.50 (5H, m), 3.78 (3H, s, diastereomer), 3.77 (3H, s, diastereomer), 3.44-3.32 (1H, m), 3.30-3.08 (1H, m), 2.64-2.56 (1H, m, diastereomer), 2.60 (1.5H, s, diastereomer), 2.42-2.32 (1H, m, diastereomer), 2.35 (1.5H, s, diastereomer), 1.14-1.00 (14H, m)

$^{13}$C NMR, (75.5 MHz, CDCl$_3$) δ 170.4, 158.6, 152.3, 150.9, 149.2, 144.4, 144.3, 141.7, 141.6, 135.5, 135.4, 135.4, 130.1, 130.1, 128.2, 128.2, 127.8, 127.0, 122.8 (2C, q, J=282.9 Hz), 122.1, 117.5, 117.3, 113.1, 95.2, 87.4, 87.3, 86.7, 86.7, 83.8, 83.2, 83.2, 78.0, 77.7, 77.6, 71.5, 71.4, 71.3, 71.1, 62.5, 61.5, 58.5, 58.3, 58.0, 57.8, 55.2, 55.2, 48.7 (1C, quintet, J=27.9 Hz), 43.4, 43.2, 43.1, 25.6, 24.7, 24.6, 24.4, 20.3, 20.2, 20.2, 20.1

$^{31}$P NMR (121.5 MHz, CDCl$_3$) δ 151.7 (0.5P, s, diastereomer), 151.6 (0.5P, s, diastereomer)

ESI TOF-MS m/z Calcd for $C_{47}H_{55}F_6N_7O_9P^+$ [M+H]$^+$ 1006.37. found 1006.39.

Example 3

(a) N$^4$-Acetyl-2'-O-(2-trifluoromethyl-3,3,3-trifluoropropanoxymethyl)-3',5'-O-(1,1,3,3-tetraisopropyldisiloxane-1,3-diyl)cytidine (1c)

[Formula 13]

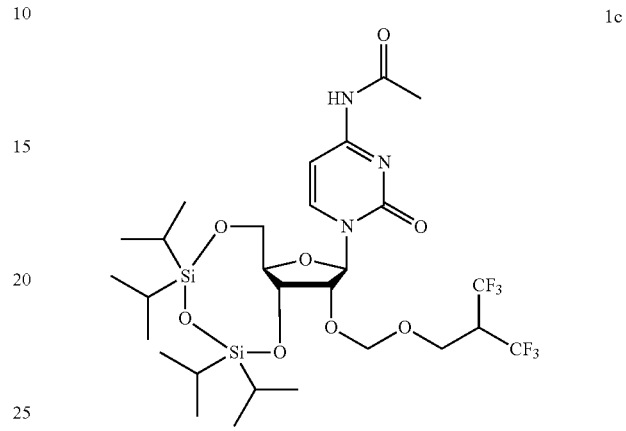

1c

This compound was synthesized in the same manner as that used for the compound 1u by using N$^4$-acetyl-2'-O-methylthiomethyl-3',5'-O-(1,1,3,3-tetraisopropyldisiloxane-1,3-diyl)cytidine instead of 2'-O-methylthiomethyl-3',5'-O-(1,1,3,3-tetraisopropyldisiloxane-1,3-diyl)uridine. Yield was 62% (white foam).

$^1$H NMR (300 MHz, CDCl$_3$) δ 9.20 (1H, brs), 8.31 (1H, d, J=7.5 Hz), 7.41 (1H, d, J=7.5 Hz), 5.77 (1H, s), 5.12 (1H, d, J=6.9 Hz), 4.98 (1H, d, J=6.9 Hz), 4.32-3.94 (7H, m), 3.50-3.34 (1H, m), 2.24 (3H, s), 1.11-0.88 (28H, m)

$^{13}$C NMR (75.5 MHz, CDCl$_3$) δ 171.2, 163.4, 154.8, 144.0, 123.1 (2C, q, J=281.5 Hz), 96.6, 94.7, 89.9, 81.9, 78.3, 67.6, 61.3, 59.3, 48.8 (1C, quintet, J=27.6 Hz), 24.7, 17.5, 17.4, 17.3, 17.2, 16.9, 16.9, 16.8, 13.2, 13.1, 12.8, 12.5

MALDI TOF-MS m/z Calcd for $C_{28}H_{45}F_6N_3NaO_8Si_2^+$ [M+Na]$^+$ 744.25. found 744.97.

(b) N$^4$-Acetyl-2'-O-(2-trifluoromethyl-3,3,3-trifluoropropanoxymethyl)-5'-O-(4,4'-dimethoxytrityl)cytidine (2c)

[Formula 14]

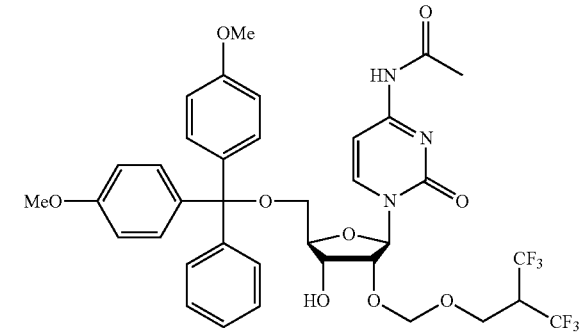

2c

This compound was synthesized in the same manner as that used for the compound 2u by using the compound 1c instead of the compound 1u. Yield was 94% (for 2 steps, white foam).

$^1$H NMR (300 MHz, CDCl$_3$) δ 9.34 (1H, brs), 8.49 (1H, d, J=7.5 Hz), 7.46-7.22 (9H, m), 7.13 (1H, d, J=7.5 Hz), 6.87 (4H, d, J=9.3 Hz), 5.94 (1H, s), 5.26 (1H, d, J=6.9 Hz), 4.93 (1H, d, J=6.9 Hz), 4.50-4.38 (1H, m), 4.24 (1H, d, J=5.1 Hz), 4.12-3.92 (3H, m), 3.81 (6H, s), 3.66 (1H, dd, J=11.3, 3.0 Hz), 3.54 (1H, dd, J=11.3, 2.4 Hz), 3.40-3.22 (1H, m), 2.45 (1H, d, J=9.6 Hz), 2.21 (3H, s)

$^{13}$C NMR (75.5 MHz, CDCl$_3$) δ 170.7, 162.9, 158.7, 158.7, 155.0, 144.6, 144.2, 135.4, 135.2, 130.1, 128.1, 128.1, 127.2, 122.9 (2C, q, J=285.2 Hz), 113.3, 96.9, 94.9, 89.5, 87.1, 82.9, 79.8, 67.8, 61.5, 60.7, 55.2, 48.8 (1C, quintet, J=27.9 Hz), 24.7

MALDI TOF-MS m/z Calcd for $C_{37}H_{37}F_6N_3NaO_9{}^+$ [M+Na]$^+$ 804.23. found 804.85.

(c) N$^4$-Acetyl-2'-O-(2-trifluoromethyl-3,3,3-trifluoropropanoxymethyl)-5'-O-(4,4'-dimethoxytrityl)cytidine 3'-O-(2-cyanoethyl N,N-diisopropylphosphoramidite) (3c)

[Formula 15]

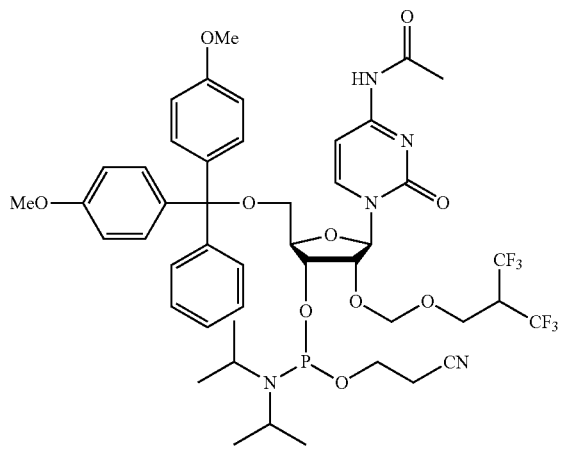

3c

This compound was synthesized in the same manner as that used for the compound 3u by using the compound 2c instead of the compound 2u. Yield was 86% (white foam).

$^1$H NMR (300 MHz, CDCl$_3$) δ 10.35 (1H, brs), 8.56 (0.7H, d, J=7.8 Hz, diastereomer), 8.49 (0.3H, d, J=7.8 Hz, diastereomer), 7.48-7.24 (9H, m), 7.05 (0.7H, d, J=7.8 Hz, diastereomer), 6.95 (0.3H, d, J=7.8 Hz, diastereomer), 6.90-6.81 (4H, m), 5.98 (1H, s), 5.08-4.96 (2H, m), 4.60-4.42 (1H, m), 4.32-3.98 (4H, m), 3.81 (4.2H, s, diastereomer), 3.80 (1.8H, s, diastereomer), 3.76-3.40 (5H, m), 2.64-2.54 (0.6H, m, diastereomer), 2.42 (1.4H, t, J=6.3 Hz, diastereomer), 2.23 (2.1H, s, diastereomer), 2.22 (0.9H, s, diastereomer), 1.21-0.96 (14H, m)

$^{13}$C NMR (75.5 MHz, CDCl$_3$) δ 170.9, 170.8, 163.2, 163.1, 158.7, 154.8, 144.5, 144.0, 143.9, 135.2, 135.1, 135.0, 135.0, 130.2, 130.2, 128.3, 127.9, 127.2, 123.2 (2C, q, J=282.1 Hz), 117.4, 117.3, 113.2, 96.9, 95.1, 94.7, 90.0, 89.9, 87.1, 87.0, 81.8, 81.7, 81.6, 81.5, 78.6, 78.4, 70.2, 69.9, 68.9, 68.7, 61.5, 61.3, 60.4, 60.2, 58.3, 58.0, 57.8, 55.2, 55.1, 48.8 (10, quintet, J=27.9 Hz), 46.1, 43.2, 43.0, 29.6, 29.3, 24.6, 24.6, 24.6, 24.5, 24.5, 24.4, 24.3, 24.3, 20.2, 20.2, 20.1

$^{31}$P NMR (121.5 MHz, CDCl$_3$) δ 152.4 (0.3P, s, diastereomer), 150.5 (0.7P, s, diastereomer); ESI TOF-MS m/z Calcd for $C_{46}H_{55}F_6N_5O_{10}P^+$ [M+H]$^+$ 982.36; found 982.43.

Example 4

(a) N$^2$-Phenoxyacetyl-2'-O-(2-trifluoromethyl-3,3,3-trifluoropropanoxymethyl)-3',5'-O-(1,1,3,3-tetraisopropyldisiloxane-1,3-diyl)guanosine (1g)

[Formula 16]

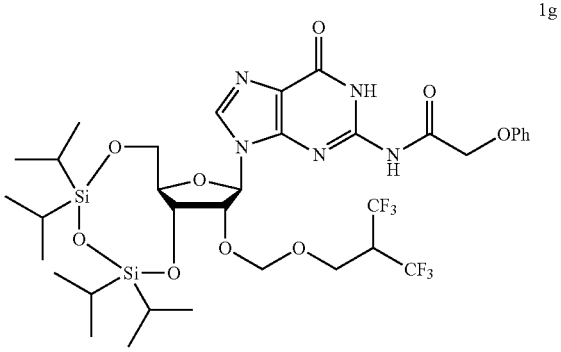

1g

This compound was synthesized in the same manner as that used for the compound 1u by using N$^2$-phenoxyacetyl-2'-O-methylthiomethyl-3',5' tetraisopropyldisiloxane-1,3-diyl)guanosine instead of 2'-O-methylthiomethyl-3',5'-O-(1,1,3,3-tetraisopropyldisiloxane-1,3-diyl)uridine. Yield was 53% (white foam).

$^1$H NMR (300 MHz, CDCl$_3$) δ 11.85 (1H, brs), 9.15 (1H, brs), 8.06 (1H, s), 7.36 (2H, t, J=7.8 Hz), 7.10 (1H, t, J=7.8 Hz), 6.97 (2H, d, J=7.8 Hz), 5.94 (1H, s), 5.08 (1H, d, J=7.2 Hz), 5.00 (1H, d, J=7.2 Hz), 4.71 (2H, s), 4.55 (1H, dd, J=9.6, 4.5 Hz), 4.38-3.92 (6H, m), 3.28-3.10 (1H, m), 1.20-0.70 (28H, m)

$^{13}$C NMR (75.5 MHz, CDCl$_3$) δ 169.6, 156.4, 155.2, 146.7, 146.3, 136.7, 130.0, 123.1, 122.9 (2C, q, J=281.5 Hz), 114.8, 94.8, 87.5, 81.4, 78.8, 68.8, 67.1, 61.4, 59.5, 48.8 (1C, quintet, J=27.9 Hz), 17.4, 17.3, 17.2, 17.0, 16.9, 16.9, 16.8, 13.3, 13.0, 12.9, 12.6

MALDI TOF-MS m/z Calcd for $C_{35}H_{49}F_6N_5NaO_9Si_2{}^+$ [M+Na]$^+$ 876.29. found 876.94.

(b) N$^2$-Phenoxyacetyl-2'-O-(2-trifluoromethyl-3,3,3-trifluoropropanoxymethyl)-5'-O-(4,4'-dimethoxytrityl)guanosine (2g)

[Formula 17]

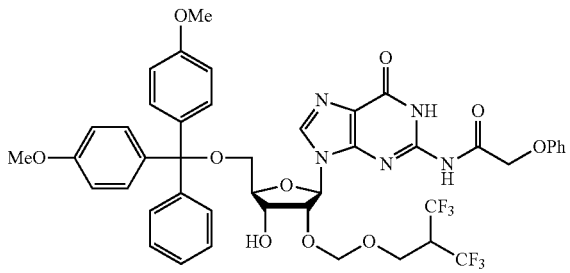

2g

This compound was synthesized in the same manner as that used for the compound 2u by using the compound 1g instead of the compound 1u. Yield was 64% (for 2 steps, white foam).

¹H NMR (300 MHz, CDCl₃) δ 11.82 (1H, brs), 9.07 (1H, brs), 7.84 (1H, s), 7.46-7.14 (11H, m), 7.08 (1H, t, J=7.5 Hz), 6.91 (2H, d, J=7.5 Hz), 6.79 (4H, d, J=8.7 Hz), 6.05 (1H, d, J=5.4 Hz), 4.83 (2H, dd, J=10.8, 7.2 Hz), 4.74 (1H, t, J=5.1 Hz), 4.62 (2H, s), 4.54-4.46 (1H, m), 4.28-4.21 (1H, m), 3.98 (1H, dd, J=11.1, 5.4 Hz), 3.82 (1H, dd, J=11.1, 4.8 Hz), 3.76 (6H, s), 3.46 (1H, dd, J=10.8, 3.0 Hz), 3.40 (1H, dd, J=10.8, 4.2 Hz), 3.20-3.02 (1H, m), 2.90 (1H, brs)

¹³C NMR (75.5 MHz, CDCl₃) δ 169.5, 158.6, 156.3, 155.2, 147.9, 146.4, 144.3, 137.3, 135.4, 135.3, 130.0, 123.0, 129.1, 128.1, 128.0, 127.1, 123.0, 122.8 (2C, q, J=282.3 Hz), 114.8, 113.2, 113.1, 95.8, 86.8, 85.7, 84.1, 80.4, 70.7, 66.8, 63.3, 61.7, 55.2, 48.7 (1C, quintet, 27.9 Hz)

MALDI TOF-MS m/z Calcd for $C_{44}H_{41}F_6N_5NaO_{10}^+$ [M+Na]⁺ 936.26. found 937.01.

(c) N²-Phenoxyacetyl-2'-O-(2-trifluoromethyl-3,3,3-trifluoropropanoxymethyl)-5'-O-(4,4'-dimethoxytrityl)guanosine 3'-O-(2-cyanoethyl N,N-diisopropylphosphoramidite) (3g)

[Formula 18]

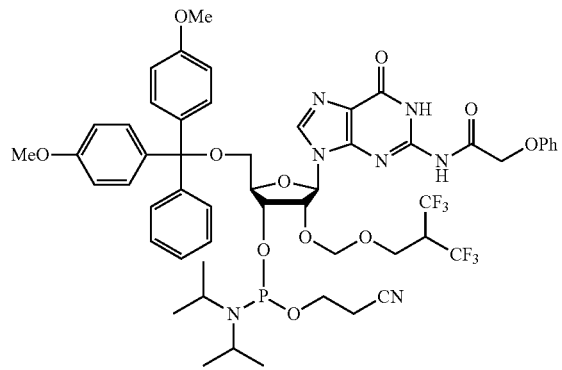

3g

This compound was synthesized in the same manner as that used for the compound 3u by using the compound 2g instead of the compound 2u. Yield was 51% (white foam).

¹H NMR (300 MHz, CDCl₃) δ 7.88 (0.5H, s, diastereomer), 7.87 (0.5H, s, diastereomer), 7.45-7.16 (11H, m), 7.07 (1H, t, J=7.5 Hz), 6.93 (1H, d, J=8.7 Hz, diastereomer), 6.88 (1H, d, J=8.7 Hz, diastereomer), 6.81 (2H, d, J=2.3 Hz, diastereomer), 6.78 (2H, d, J=2.3 Hz, diastereomer), 6.07 (0.5H, d, J=6.0 Hz, diastereomer), 6.01 (0.5H, d, J=6.3 Hz, diastereomer), 4.92-4.78 (2H, m), 4.75-4.68 (1H, m), 4.63-4.54 (2H, m), 4.41-4.35 (0.5H, m, diastereomer), 4.32-4.35 (0.5H, m, diastereomer), 4.04-3.28 (7H, m), 3.77 (6H, s), 3.18-3.00 (1H, m), 2.65 (1H, t, J=6.3 Hz, diastereomer), 2.35 (1H, t, J=6.3 Hz, diastereomer), 1.44-1.00 (14H, m)

¹³C NMR (75.5 MHz, CDCl₃) δ 169.7, 169.5, 158.6, 156.5, 156.5, 155.6, 148.1, 146.7, 146.6, 144.3, 144.2, 137.5, 137.2, 135.5, 135.4, 135.2, 130.1, 130.0, 130.0, 129.9, 128.2, 128.0, 128.0, 127.9, 127.1, 122.8 (2C, q, J=279.7 Hz), 122.8, 122.8, 122.2, 122.0, 117.5, 117.3, 114.8, 113.2, 113.2, 95.2, 95.1, 86.8, 86.7, 85.8, 85.7, 84.2, 83.8, 83.8, 78.6, 77.8, 77.7, 71.9, 71.7, 71.4, 71.2, 66.9, 63.1, 61.6, 58.7, 58.5, 57.8, 57.5, 55.2, 55.2, 52.8, 48.6 (1C, quintet, J=27.9 Hz), 45.9, 43.4, 43.2, 43.0, 29.7, 24.7, 24.6, 24.5, 24.4, 20.3, 20.2, 20.1, 20.1

³¹P NMR (121.5 MHz, CDCl₃) δ 151.7 (0.5P, s, diastereomer), 151.6 (0.5P, s, diastereomer); ESI TOF-MS m/z Calcd for $C_{53}H_{59}F_6N_7O_{11}P^+$ [M+H]⁺ 1114.39; found 1114.50.

Example 5

(a) 5'-O-(4,4'-dimethoxytrityl)-2'-O-,3'-O-bis(benzyloxycarbonyl)uridine (4u)

[Formula 19]

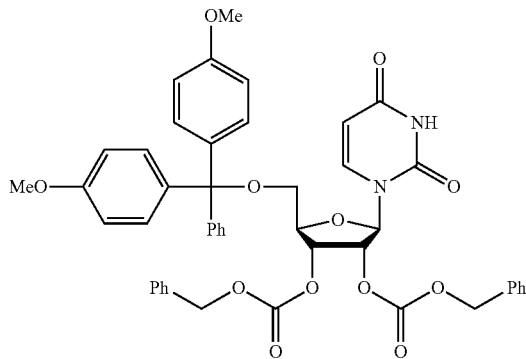

4u

To a solution of 5'-O-(4,4'-dimethoxytrityl)uridine (300 mg, 500 μmol) in dichloromethane/5% aqueous NaHCO₃ (1:1, v/v, 5 mL) was added Z-NT (400 mg, 1.5 mmol) and i-Pr₂NEt (900 μL, 5.0 mmol), and the mixture was stirred for 1 hour. The reaction mixture was diluted with dichloromethane (10 mL), and washed with 5% aqueous NaHCO₃ (3×10 mL). The aqueous layer was back-extracted with dichloromethane (10 mL), and the combined organic layer was dried over Na₂SO₄, filtered to separate Na₂SO₄, and dried under reduced pressure. The residue was purified by silica gel chromatography (eluent: 0 to 2% methanol in dichloromethane) to give the objective compound 4u (370 mg, 93%) as white foam.

¹H NMR (300 MHz, CDCl₃) δ 7.91 (1H, brs), 7.70 (1H, d, J=8.4 Hz), 7.40-7.22 (19H, m), 6.88-6.81 (4H, m), 6.23 (1H, d, J=5.4 Hz), 5.56-5.46 (2H, m), 5.33-5.27 (1H, m), 5.19 (1H, d, J=12.0 Hz), 5.14 (1H, d, J=12.0 Hz), 5.12 (2H, s), 4.32-4.28 (1H, m), 3.80 (6H, s), 3.58-3.42 (2H, m).

(b) 2'-O-,3'-O-Bis(benzyloxycarbonyl)uridine (5u)

[Formula 20]

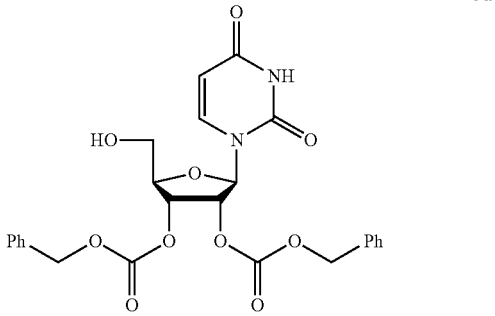

5u

To a solution of the compound 4u (370 mg, 460 μmol) in dichloromethane (50 mL) was added DCA (1.5 mL). The mixture was stirred for 10 minutes, and washed with 5% aqueous NaHCO₃ (3×50 mL). The aqueous layer was back-extracted with dichloromethane (10 mL), and the combined organic layer was dried over Na₂SO₄, filtered to separate Na₂SO₄, and dried under reduced pressure. The residue was purified by silica gel chromatography (eluent: 0 to 4% methanol in dichloromethane) to give the objective compound 5u (200 mg, 87%) as white foam.

¹H NMR (300 MHz, CDCl₃) δ 8.48 (1H, brs), 7.52 (1H, d, J=8.2 Hz), 7.37-7.33 (10H, m), 5.86 (1H, d, J=6.0 Hz), 5.75 (1H, d, J=8.2 Hz), 5.59 (1H, dd, J=6.0, 5.4 Hz), 5.45 (1H, dd, J=5.4, 3.0 Hz), 5.13 (2H, s), 5.12 (2H, d, J=0.6 Hz), 4.32-4.26 (1H, m), 4.00-3.78 (2H, m), 2.94-2.86 (1H, m).

(c) 2-Cyanoethyl 5'-O-(4,4'-dimethoxytrityl)-2'-O-(2-trifluoromethyl-3,3,3-trifluoropropanoxymethyl) uridin-3'-yl 2'-O,3'-O-bis(benzyloxycarbonyl)uridin-5'-yl phosphate (6uu)

[Formula 21]

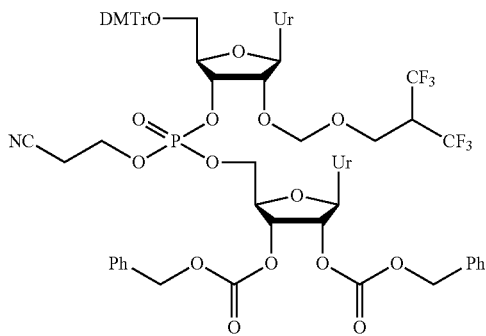

6uu

The compound 3u (52.7 mg, 56 μmol) and the compound 5u (24.6 mg, 48 μmol) were dried by repeated coevaporation with dry toluene, and finally dissolved in dry acetonitrile (500 μL). To the solution, tetrazole (7.9 mg, 114 μmol) was added, and the reaction was allowed at room temperature for 3 hours. tert-Butyl hydroperoxide (40 μL, 70% in water) was then added to the reaction mixture, and the mixture was further stirred for 30 minutes. The reaction mixture was diluted with dichloromethane (25 mL), and washed with 5% aqueous NaHCO₃ (2×25 mL). The aqueous layer was back-extracted with dichloromethane (2×25 mL), and the combined organic layer was dried over Na₂SO₄, filtered to separate Na₂SO₄, and dried under reduced pressure. The residue was purified by silica gel chromatography (eluent: 0 to 4% methanol in dichloromethane, containing 0.5% pyridine) to give the objective compound 6uu (52.9 mg, 81%) as white foam.

¹H NMR (300 MHz, CDCl₃) δ 9.65-9.50 (2H, m), 7.78 (1H, d, J=7.8 Hz), 7.40-7.15 (19H, m), 7.09 (1H, d, J=8.1 Hz), 6.90-6.80 (4H, m), 6.01 (1H, t, J=4.8 Hz), 5.82-5.52 (2H, m), 5.51-5.42 (2H, m), 5.34-5.26 (1H, m), 5.16-4.98 (4H, m), 4.96-4.78 (2H, m), 4.64-4.54 m), 4.44-3.90 (9H, m), 3.82-3.52 (6H, m), 3.64-3.46 (2H, m), 3.34-3.14 (1H, m), 2.80-2.52 (21-1,

³¹P NMR (121.5 MHz, CDCl₃) δ−1.5 (0.5P, s, diastereomer), −1.7 (0.5P, s, diastereomer).

(d) 2-Cyanoethyl 2'-O-(2-trifluoromethyl-3,3,3-trifluoropropanoxymethyl)uridin-3'-yl 2'-O,3'-O-bis(benzyloxycarbonyl)uridin-5'-yl phosphate (7uu)

[Formula 22]

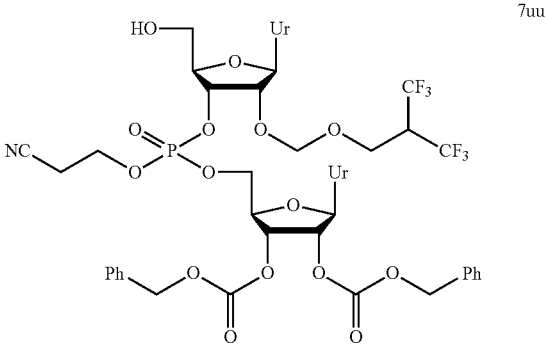

7uu

To a solution of the compound 6uu (52.9 mg, 39 μmol) in dichloromethane (4 mL) was added DCA (120 μL). The mixture was stirred at room temperature for 15 minutes, and washed with 5% aqueous NaHCO₃ (2×5 mL). The aqueous layer was back-extracted with dichloromethane (5 mL), and the combined organic layer was dried over Na₂SO₄, filtered to separate Na₂SO₄, and dried under reduced pressure. The residue was purified by silica gel chromatography (eluent: 1 to 4% methanol in dichloromethane) to give the objective compound 7uu (33.0 mg, 79%) as white foam.

¹H NMR (300 MHz, CDCl₃) δ 10.26-9.84 (2H, m), 7.88 (0.5H, d, J=8.1 Hz, diastereomer), 7.85 (0.5H, d, J=8.7 Hz, diastereomer), 7.36-7.26 (11H, m), 5.94 (0.5H, d, J=5.4 Hz, diastereomer), 5.91 (0.5H, d, J=4.8 Hz, diastereomer), 5.80-5.48 (5H, m), 5.18-5.00 (4H, m), 4.90-4.77 (2H, m), 4.68-4.22 (7H, m), 4.08-3.76 (4H, m), 3.40-3.22 (1H, m), 2.81-2.67 (2H, m), 2.09 (1H, brs)

³¹P NMR (121.5 MHz, CDCl₃) δ−0.9 (0.5P, s, diastereomer), −2.5 (0.5P, s, diastereomer).

(e) 2-Cyanoethyl 2'-O-(2-trifluoromethyl-3,3,3-trifluoropropanoxymethyl)uridin-3'-yl uridin-5'-yl phosphate (8uu)

[Formula 23]

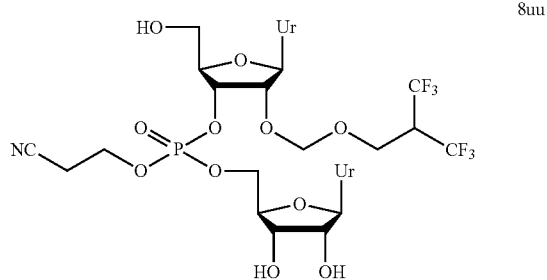

8uu

To a solution of the compound 7uu (55.0 mg, 51.6,umol) in methanol (1.0 mL) was added 20% Pd(OH)₂/C (10 mg), and the mixture was vigorously stirred overnight at room temperature under a hydrogen atmosphere. The reaction mixture was filtered through a Celite pad, and the filtrate was dried under reduced pressure to give the objective compound 8uu (40 mg, 97%) as white foam $^1$H NMR (300 MHz, CD$_3$OD) δ 8.03 (0.5H, d., J=2.1 Hz, diastereomers), 8.01 (0.5H, d, J=1.8 Hz, diastereomers), 7.71 (0.5H, d, J=7.8 Hz, diastereomers), 7.67 (0.5H, d, J=7.8 Hz, diastereomers), 6.20-6.08 (1H, m), 5.90-5.70 (3H, m), 5.12-5.04 (1H, m), 4.92-4.82 (1H, m), 4.64-4.28 (10H, m), 4.26-4.10 (2H, m), 4.10-3.86 (2H, m), 3.86-3.68 (2H, m), 3.34-3.28 (1H, m), 2.98-2.88 (2H, m), 1.29 (1H, brs)

MALDI TOF-MS m/z Calcd for $C_{26}H_{30}F_6N_5NaO_{15}P^+$ [M+Na]$^+$ 820.13. found 820.30.

Example 6

N$^6$-Acetyl 2'-O-(2-trifluoromethyl-3,3,3-trifluoro-propanoxymethyl)-5'-O-(4,4'-dimethoxytrityl)adenosine 3'-O-((3S,3aR)-3-phenylhexahydropyrrolo[1,2-c][1,3,2]oxazaphosphol-1-yl) ((Sp)-9a)

[Formula 24]

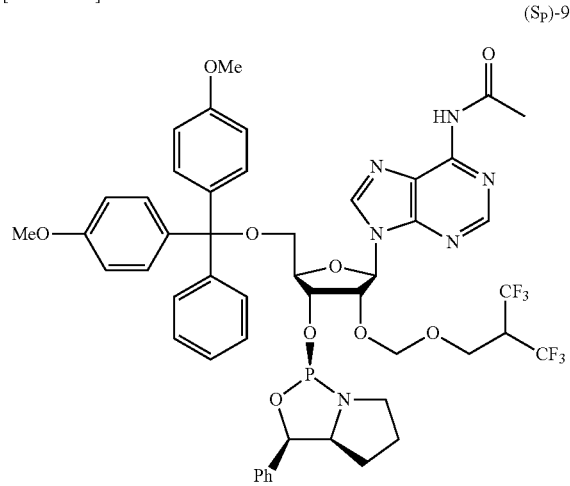

(Sp)-9a

The compound 2a (163.8 mg, 200 μmol) was dried by repeated co-evaporations with dry pyridine and dry toluene, and dissolved in dry tetrahydrofuran (600 μL). Et$_3$N (141 μL, 1 mmol) and a solution of (3S,3aR)-1-chloro-3-phenyl-hexahydropyrrolo[1,2-c][1,3,2]oxazaphosphole (0.5 M solution in tetrahydrofuran, 800 μL, 400 μmol) were successively added dropwise to the solution at −78° C. with stirring. The mixture was stirred at room temperature for 40 minutes, then poured into ice-cooled saturated aqueous NaHCO$_3$ (20 mL), and extracted with chloroform (20 mL). The organic layer was washed with ice-cooled saturated aqueous NaHCO$_3$ (2×20 mL), and the combined aqueous layer was back-extracted with chloroform (20 mL). The combined organic layer was dried over Na$_2$SO$_4$, filtered to separate Na$_2$SO$_4$, and dried under reduced pressure. The residue was purified by silica gel chromatography (eluent: ethyl acetate:n-hexane=1:3, containing 0.5% Et$_3$N) to afford the objective compound (Sp)-9a (130.4 mg, 63%) as white foam.

$^1$H NMR (300 MHz, CDCl$_3$) δ 8.58 (1H, s), 8.23 (1H, s), 7.50-7.12 (14H, m), 6.80 (4H, d, J=9.0 Hz), 6.21 (1H, d, J=4.2 Hz), 5.77 (1H, d, J=6.3 Hz), 5.04-4.86 (1H, m), 4.82 (1H, d, J=7.2 Hz), 4.69 (1H, d, J=7.2 Hz), 4.44-4.32 (1H, m), 3.92-3.36 (5H, m), 3.78 (6H, s), 3.18-2.98 (2H, m), 2.61 (3H, s), 1.80-1.50 (2H, m), 1.34-0.78 (4H, m)

$^{31}$P NMR (121.5 MHz, CDCl$_3$) δ 157.2.

Example 7

By using the compound 1u or the compound 2u obtained in Example 1, elimination conditions of the protective group were examined. The substrate concentration was 0.1 M, provided that the substrate concentration for the reaction numbers 4, 5, 7 and 8 was 10 mM. The reactions were performed at room temperature, and advance of the reactions was confirmed by thin layer chromatography. The reaction conditions and the results are shown in Table 1 (in the table, Me represents methoxy group, TBAF represents tetrabutylammonium fluoride, THF represents tetrahydrofuran, DBU represents 1,8-diazabicyclo[5.4.0]undec-7-ene, TMSCl represents trimethylsilyl chloride, EtOH represents ethanol, Et$_3$N represents triethylamine, DCA represents dichloroacetic acid, DCM represents dichloromethane, and TFA represents trifluoroacetic acid). The results shown in Table 1 revealed that the protective group of the present invention could be extremely quickly removed under mild conditions by allowing a fluorine compound such as tetrabutylammonium fluoride to act on it, and was stable under acidic conditions.

TABLE 1

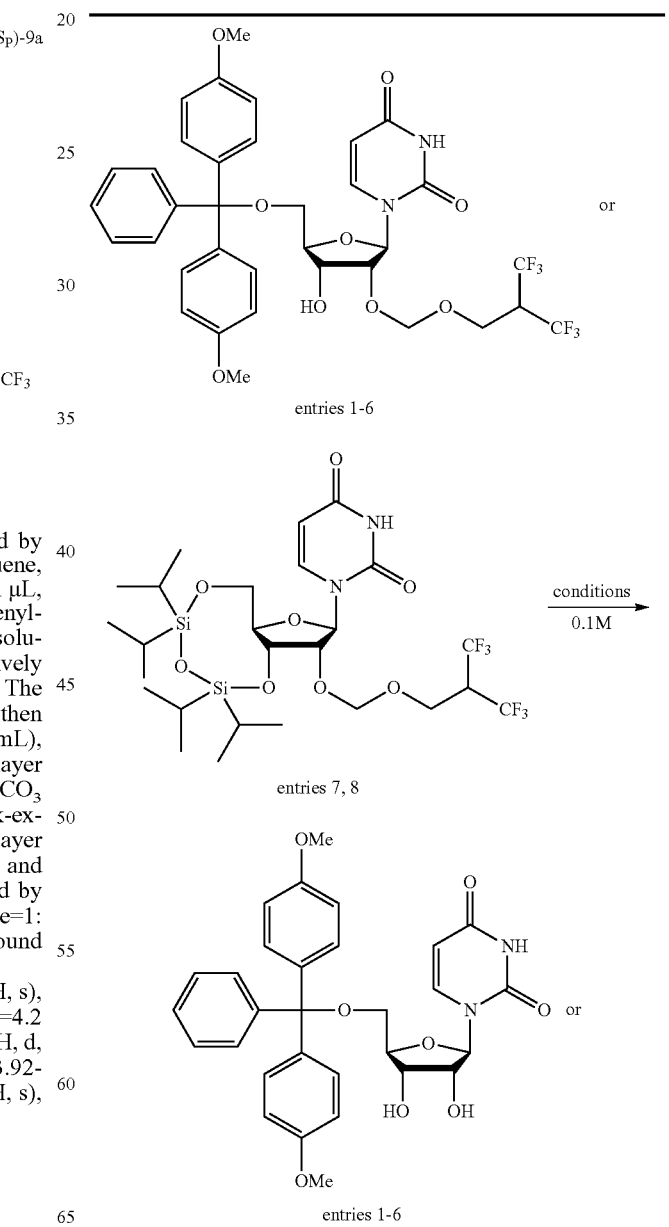

TABLE 1-continued

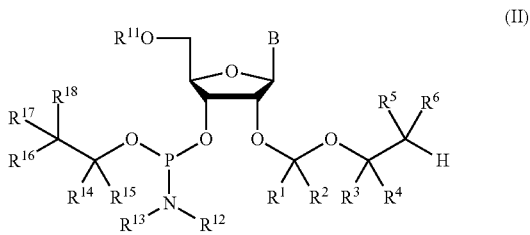

entries 7, 8

| entry | conditions | results [a] |
|---|---|---|
| 1 | 1M TBAF/THF | 100% deprotected (<1 min) |
| 2 | 0.5M DBU/CH$_3$CN | 100% deprotected (2 h) |
| 3 | 0.5M DBU/CH$_3$CN—TMSCl (9:1, v/v) | 100% deprotected (30 min) |
| 4 [b] | conc. NH$_3$—EtOH (3:1, v/v) | 100% deprotected (1 h) |
| 5 [b] | 2M NH$_3$/EtOH | rt, stable |
| 6 | 1M Et$_3$N-3HF | stable (>1 day) |
| 7 [b] | 3% DCA/DCM | stable (>1 day) |
| 8 [b] | 1% TFA/DCM | 5% deprotected (12 h) |

INDUSTRIAL APPLICABILITY

The protective group represented by the aforementioned general formula (I) is stable under the reaction conditions of the nucleic acid synthetics cycles and has little steric hindrance, and can be very efficiently removed in a short time by treatment with, for example, a fluorine compound under mild conditions. Therefore, the group has ideal characteristics as a protective group for the 2'-hydroxyl group of a ribonucleoside, a ribonucleotide, or a derivative thereof, and can be used for industrial nucleic acid synthesis.

What is claimed is:

1. A protective group for 2'-hydroxyl group of a ribonucleoside or ribonucleotide, which is represented by the following general formula (I):

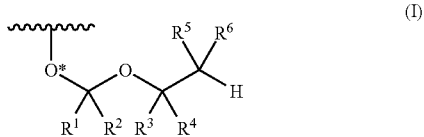

wherein, the oxygen atom attached with * represents an oxygen atom of the 2'-hydroxyl group of a ribonucleoside or ribonucleotide; $R^1$ and $R^2$ both represent a hydrogen atom, or independently represent a halogen atom, a $C_{1-6}$ alkyl group, or a $C_{1-6}$ halo-substituted alkyl group; $R^3$ and $R^4$ independently represent a hydrogen atom, a halogen atom, a $C_{1-6}$ alkyl group, or a $C_{1-6}$ halo-substituted alkyl group; and $R^5$ and $R^6$ represent the same fluoro-substituted $C_{1-6}$ alkyl group or the same perfluoro($C_{1-6}$ alkyl) group.

2. The protective group according to claim 1, wherein both $R^1$ and $R^2$ are hydrogen atoms.

3. The protective group according to claim 1, wherein both $R^3$ and $R^4$ are hydrogen atoms.

4. The protective group according to claim 1, wherein $R^5$ and $R^6$ represent the same fluoro-substituted $C_{1-6}$ alkyl group.

5. The protective group according to claim 1, wherein $R^5$ and $R^6$ represent the same perfluoro($C_{1-6}$ alkyl) group.

6. The protective group according to claim 1, wherein both $R^5$ and $R^6$ are trifluoromethyl groups.

7. The protective group according to claim 1, wherein the ribonucleoside or ribonucleotide is a phosphoroamidite compound.

8. A ribonucleoside or a ribonucleotide, wherein the oxygen atom of the 2'-hydroxyl group is protected with the protective group according to claim 1.

9. The ribonucleoside or ribonucleotide according to claim 8, which is a phosphoroamidite compound.

10. The ribonucleoside or ribonucleotide according to claim 9, wherein the phosphoroamidite compound is a compound represented by the following general formula (II):

(II)

$R^{11}O$—[structure with B, and phosphoramidite group containing $R^{17}$, $R^{18}$, $R^{16}$, $R^{14}$, $R^{15}$, $R^{13}$, $R^{12}$, $R^1$, $R^2$, $R^3$, $R^4$, $R^5$, $R^6$]

wherein, B represents a natural or non-natural nucleobase which may have a protective group; $R^1$, $R^2$, $R^3$, $R^4$, $R^5$, and $R^6$ have the same meanings as those defined above; $R^{11}$ represents a trityl group which optionally has a substituent, or a trityl group in which two phenyl groups among the three phenyl groups constituting the trityl group bind to each other via an oxygen atom to form a xanthene ring; $R^{12}$ and $R^{13}$ independently represent a $C_{1-6}$ alkyl group, or $R^{12}$ and $R^{13}$ bind to each other to form a saturated 5- or 6-membered ring, the ring constituting atoms optionally containing one or two or more oxygen atoms or sulfur atoms; $R^{14}$ and $R^{15}$ independently represent a hydrogen atom or a $C_{1-6}$ alkyl group, provided that $R^{14}$ may bind to $R^{13}$ to form a 5- or 6-membered ring; $R^{16}$ represents an electron withdrawing group, or when $R^{14}$ binds to $R^{13}$ to form a 5- or 6-membered ring, $R^{16}$ represents an electron withdrawing group or a hydrogen atom; and $R^{17}$ and $R^{18}$ represent a hydrogen atom or a $C_{1-6}$ alkyl group, or $R^{16}$, $R^{17}$, and $R^{18}$ bind to one another to represent an aryl group together with the carbon atoms to which they bind.

11. The ribonucleoside or ribonucleotide according to claim 10 which is a compound represented by the following formula (IIA):

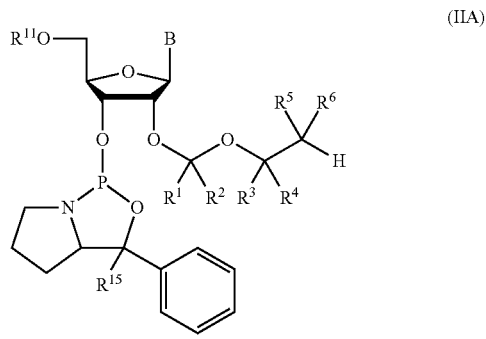

wherein the symbols have the same meanings as those defined above.

12. A method for preparing an oligoribonucleic acid, comprising reacting the phosphoroamidite compound according to claim 10 in a reaction for synthesizing the oligoribonucleic acid.

13. A method for introducing a protective group for a 2'-hydroxyl group of a ribonucleoside or ribonucleotide, which is represented by the following general formula (I):

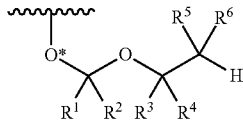
(I)

wherein, the oxygen atom attached with * represents an oxygen atom of the 2'-hydroxyl group of a ribonucleoside or ribonucleotide; $R^1$ and $R^2$ both represent a hydrogen atom, or independently represent a halogen atom, a $C_{1-6}$ alkyl group, or a $C_{1-6}$ halo-substituted alkyl group; $R^3$ and $R^4$ independently represent a hydrogen atom, a halogen atom, a $C_{1-6}$ alkyl group, or a $C_{1-6}$ halo-substituted alkyl group; and $R^5$ and $R^6$ represent the same fluoro-substituted $C_{1-6}$ alkyl group or the same perfluoro($C_{1-6}$ alkyl) group, wherein the method comprises reacting a reagent comprising a compound represented by the following general formula (III):

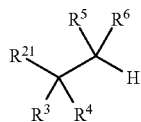
(III)

wherein, $R^3$, $R^4$, $R^5$, and $R^6$ have the same meanings as those defined above, and $R^{21}$ represents a hydroxyl group, with a ribonucleoside or a ribonucleotide of which the 2'-hydroxyl group is protected with a $C_{1-6}$ alkylthiomethyl group.

14. A method for introducing the protective group for a 2'-hydroxyl group of a ribonucleoside or a ribonucleotide, which is represented by the following general formula (I):

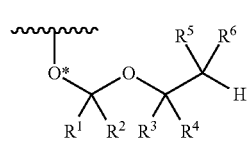
(I)

wherein, the oxygen atom attached with * represents oxygen atom of 2'-hydroxyl group of a ribonucleoside, a ribonucleotide or a derivative thereof; $R^1$ and $R^2$ both represent hydrogen atom, or independently represent a halogen atom, a $C_{1-6}$ alkyl group, or a $C_{1-6}$ halo-substituted alkyl group; $R^3$ and $R^4$ independently represent hydrogen atom, a halogen atom, a $C_{1-6}$ alkyl group, or a $C_{1-6}$ halo-substituted alkyl group; and $R^5$ and $R^6$ represent the same fluoro-substituted $C_{1-6}$ alkyl group or the same perfluoro($C_{1-6}$ alkyl) group, wherein the method comprises reacting a reagent comprising a compound represented by the following general formula (III):

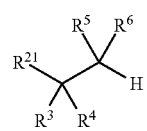
(III)

wherein, $R^3$, $R^4$, $R^5$, and $R^6$ have the same meanings as those defined above, $R^{21}$ represents $R^{22}$—S—C($R^1$)($R^2$)—O—, wherein in the formula $R^{22}$ represents a $C_{1-6}$ alkyl group, and $R^1$ and $R^2$ have the same meanings as those defined above, or X—C($R^1$)($R^2$)—O—, wherein in the formula, X represents a leaving group, and $R^1$ and $R^2$ have the same meanings as those defined above, with a ribonucleoside or ribonucleotide of which the 2'-hydroxyl group is not protected.

* * * * *